(12) United States Patent
Spivey et al.

(10) Patent No.: US 8,037,591 B2
(45) Date of Patent: Oct. 18, 2011

(54) SURGICAL SCISSORS

(75) Inventors: James T. Spivey, Cincinnati, OH (US); Thomas T. Washburn, Concord, MA (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 262 days.

(21) Appl. No.: 12/364,172

(22) Filed: Feb. 2, 2009

(65) Prior Publication Data
US 2010/0198244 A1    Aug. 5, 2010

(51) Int. Cl.
*B23P 11/00* (2006.01)
*A61B 17/32* (2006.01)

(52) U.S. Cl. ...................... 29/525.01; 606/174

(58) Field of Classification Search ............... 29/525.01, 29/525.14, 468, 446, 428, 464, 718, 721, 29/757, 758, 759, 760, 238, 270, 271, 281.6; 606/174, 170, 51, 56, 46; 72/305
See application file for complete search history.

(56) References Cited

U.S. PATENT DOCUMENTS

| | | |
|---|---|---|
| 645,576 A | 3/1900 | Tesla |
| 649,621 A | 5/1900 | Tesla |
| 787,412 A | 4/1905 | Tesla |
| 1,127,948 A | 2/1915 | Wappler |
| 1,482,653 A | 2/1924 | Lilly |
| 1,625,602 A | 4/1927 | Gould et al. |
| 2,028,635 A | 1/1936 | Wappler |
| 2,113,246 A | 4/1938 | Wappler |
| 2,155,365 A | 4/1939 | Rankin |
| 2,191,858 A | 2/1940 | Moore |
| 2,196,620 A | 4/1940 | Attarian |
| 2,388,137 A | 10/1945 | Graumlich |
| 2,493,108 A | 1/1950 | Casey, Jr. |
| 2,504,152 A | 4/1950 | Riker et al. |
| 2,952,206 A | 9/1960 | Becksted |
| 3,069,195 A | 12/1962 | Buck |
| 3,170,471 A | 2/1965 | Schnitzer |
| 3,435,824 A | 4/1969 | Gamponia |
| 3,470,876 A | 10/1969 | Barchilon |
| 3,669,487 A | 6/1972 | Roberts et al. |
| 3,746,881 A | 7/1973 | Fitch et al. |

(Continued)

FOREIGN PATENT DOCUMENTS

DE    3008120 A1    9/1980

(Continued)

OTHER PUBLICATIONS

Michael S. Kavic, M.D., "Natural Orifice Translumenal Endoscopic Surgery: "NOTES"", JSLS, vol. 10, pp. 133-134 (2006).

(Continued)

*Primary Examiner* — John C Hong

(57) ABSTRACT

Surgical scissors devices are disclosed. The surgical scissors devices may comprise an end effector with first and second blade members. The first and second blade members may respectively comprise proximally positioned cams and distally positioned blade ends. Also, the first and second blade members may be coupled at a pivot point by a fastener held in tension along its longitudinal axis by the blade members. A reciprocating shuttle may comprise at least one pin positioned within slots defined by the respective cams of the blade members. Distally-directed motion of the shuttle may cause the first and second blade members to open and proximally-directed motion of the shuttle may cause the first and second blade members to close. Methods and apparatuses for forming the surgical scissors device are also disclosed.

28 Claims, 20 Drawing Sheets

U.S. PATENT DOCUMENTS

| | | | |
|---|---|---|---|
| 3,799,672 A | 3/1974 | Vurek |
| 3,946,740 A | 3/1976 | Bassett |
| 3,994,301 A | 11/1976 | Agris |
| 4,011,872 A | 3/1977 | Komiya |
| 4,012,812 A | 3/1977 | Black |
| 4,164,225 A | 8/1979 | Johnson et al. |
| 4,178,920 A | 12/1979 | Cawood, Jr. et al. |
| 4,207,873 A | 6/1980 | Kruy |
| 4,235,238 A | 11/1980 | Ogiu et al. |
| 4,258,716 A | 3/1981 | Sutherland |
| 4,278,077 A | 7/1981 | Mizumoto |
| 4,285,344 A | 8/1981 | Marshall |
| 4,311,143 A | 1/1982 | Komiya |
| 4,396,021 A | 8/1983 | Baumgartner |
| 4,452,246 A | 6/1984 | Bader et al. |
| 4,461,281 A | 7/1984 | Carson |
| 4,491,132 A | 1/1985 | Aikins |
| 4,527,331 A | 7/1985 | Lasner et al. |
| 4,527,564 A | 7/1985 | Eguchi et al. |
| 4,538,594 A | 9/1985 | Boebel et al. |
| D281,104 S | 10/1985 | Davison |
| 4,580,551 A | 4/1986 | Siegmund et al. |
| 4,646,722 A | 3/1987 | Silverstein et al. |
| 4,653,476 A | 3/1987 | Bonnet |
| 4,669,470 A | 6/1987 | Brandfield |
| 4,671,477 A | 6/1987 | Cullen |
| 4,685,447 A | 8/1987 | Iversen et al. |
| 4,711,240 A | 12/1987 | Goldwasser et al. |
| 4,712,545 A | 12/1987 | Honkanen |
| 4,721,116 A | 1/1988 | Schintgen et al. |
| 4,733,662 A | 3/1988 | DeSatnick et al. |
| D295,894 S | 5/1988 | Sharkany et al. |
| 4,763,669 A | 8/1988 | Jaeger |
| 4,770,188 A | 9/1988 | Chikama |
| 4,823,794 A | 4/1989 | Pierce |
| 4,829,999 A | 5/1989 | Auth |
| 4,873,979 A | 10/1989 | Hanna |
| 4,880,015 A | 11/1989 | Nierman |
| 4,911,148 A | 3/1990 | Sosnowski et al. |
| 4,926,860 A | 5/1990 | Stice et al. |
| 4,938,214 A | 7/1990 | Specht et al. |
| 4,950,273 A | 8/1990 | Briggs |
| 4,950,285 A | 8/1990 | Wilk |
| 4,984,581 A | 1/1991 | Stice |
| 5,007,917 A | 4/1991 | Evans |
| 5,010,876 A | 4/1991 | Henley et al. |
| 5,020,514 A | 6/1991 | Heckele |
| 5,020,535 A | 6/1991 | Parker et al. |
| 5,025,778 A | 6/1991 | Silverstein et al. |
| 5,033,169 A | 7/1991 | Bindon |
| 5,037,433 A | 8/1991 | Wilk et al. |
| 5,041,129 A | 8/1991 | Hayhurst et al. |
| 5,046,513 A | 9/1991 | Gatturna et al. |
| 5,050,585 A | 9/1991 | Takahashi |
| 5,065,516 A | 11/1991 | Dulebohn |
| 5,066,295 A | 11/1991 | Kozak et al. |
| 5,123,913 A | 6/1992 | Wilk et al. |
| 5,123,914 A | 6/1992 | Cope |
| 5,133,727 A | 7/1992 | Bales et al. |
| 5,174,300 A | 12/1992 | Bales et al. |
| 5,176,126 A | 1/1993 | Chikama |
| 5,190,050 A | 3/1993 | Nitzsche |
| 5,190,555 A | 3/1993 | Wetter et al. |
| 5,192,284 A | 3/1993 | Pleatman |
| 5,201,752 A | 4/1993 | Brown et al. |
| 5,201,908 A | 4/1993 | Jones |
| 5,203,785 A | 4/1993 | Slater |
| 5,203,787 A | 4/1993 | Noblitt et al. |
| 5,209,747 A | 5/1993 | Knoepfler |
| 5,217,003 A | 6/1993 | Wilk |
| 5,217,453 A | 6/1993 | Wilk |
| 5,219,357 A | 6/1993 | Honkanen et al. |
| 5,219,358 A | 6/1993 | Bendel et al. |
| 5,222,362 A | 6/1993 | Maus et al. |
| 5,222,965 A | 6/1993 | Haughton |
| 5,234,453 A | 8/1993 | Smith et al. |
| 5,235,964 A | 8/1993 | Abenaim |
| 5,242,456 A | 9/1993 | Nash et al. |
| 5,246,424 A | 9/1993 | Wilk |
| 5,259,366 A | 11/1993 | Reydel et al. |
| 5,263,958 A | 11/1993 | deGuillebon et al. |
| 5,273,524 A | 12/1993 | Fox et al. |
| 5,275,607 A | 1/1994 | Lo et al. |
| 5,284,128 A | 2/1994 | Hart |
| 5,284,162 A | 2/1994 | Wilk |
| 5,287,845 A | 2/1994 | Faul et al. |
| 5,290,299 A | 3/1994 | Fain et al. |
| 5,290,302 A | 3/1994 | Pericic |
| 5,295,977 A | 3/1994 | Cohen et al. |
| 5,297,536 A | 3/1994 | Wilk |
| 5,301,061 A | 4/1994 | Nakada et al. |
| 5,312,351 A | 5/1994 | Gerrone |
| 5,312,416 A | 5/1994 | Spaeth et al. |
| 5,312,423 A | 5/1994 | Rosenbluth et al. |
| 5,320,636 A | 6/1994 | Slater |
| 5,325,845 A | 7/1994 | Adair |
| 5,330,471 A | 7/1994 | Eggers |
| 5,330,486 A | 7/1994 | Wilk |
| 5,330,488 A | 7/1994 | Goldrath |
| 5,330,496 A | 7/1994 | Alferness |
| 5,330,502 A | 7/1994 | Hassler et al. |
| 5,331,971 A | 7/1994 | Bales et al. |
| 5,334,198 A | 8/1994 | Hart et al. |
| 5,344,428 A | 9/1994 | Griffiths |
| 5,350,391 A | 9/1994 | Iacovelli |
| 5,352,184 A | 10/1994 | Goldberg et al. |
| 5,352,222 A | 10/1994 | Rydell |
| 5,354,302 A | 10/1994 | Ko |
| 5,354,311 A | 10/1994 | Kambin et al. |
| 5,356,408 A | 10/1994 | Rydell |
| 5,364,408 A | 11/1994 | Gordon |
| 5,364,410 A | 11/1994 | Failla et al. |
| 5,366,466 A | 11/1994 | Christian et al. |
| 5,366,467 A | 11/1994 | Lynch et al. |
| 5,368,605 A | 11/1994 | Miller, Jr. |
| 5,370,647 A | 12/1994 | Graber et al. |
| 5,374,273 A | 12/1994 | Nakao et al. |
| 5,374,275 A | 12/1994 | Bradley et al. |
| 5,374,277 A | 12/1994 | Hassler |
| 5,377,695 A | 1/1995 | An Haack |
| 5,383,877 A | 1/1995 | Clarke |
| 5,383,888 A | 1/1995 | Zvenyatsky et al. |
| 5,391,174 A | 2/1995 | Weston |
| 5,392,789 A | 2/1995 | Slater et al. |
| 5,395,386 A | 3/1995 | Slater |
| 5,401,248 A | 3/1995 | Bencini |
| 5,403,328 A | 4/1995 | Shallman |
| 5,403,342 A | 4/1995 | Tovey et al. |
| 5,403,348 A | 4/1995 | Bonutti |
| 5,405,073 A | 4/1995 | Porter |
| 5,405,359 A | 4/1995 | Pierce |
| 5,409,478 A | 4/1995 | Gerry et al. |
| 5,417,699 A | 5/1995 | Klein et al. |
| 5,423,821 A | 6/1995 | Pasque |
| 5,433,721 A | 7/1995 | Hooven et al. |
| 5,439,471 A | 8/1995 | Kerr |
| 5,439,478 A | 8/1995 | Palmer |
| 5,441,059 A | 8/1995 | Dannan |
| 5,441,499 A | 8/1995 | Fritzsch |
| 5,449,021 A | 9/1995 | Chikama |
| 5,456,684 A | 10/1995 | Schmidt et al. |
| 5,458,131 A | 10/1995 | Wilk |
| 5,458,583 A | 10/1995 | McNeely et al. |
| 5,460,168 A | 10/1995 | Masubuchi et al. |
| 5,460,629 A | 10/1995 | Shlain et al. |
| 5,462,561 A | 10/1995 | Voda |
| 5,465,731 A | 11/1995 | Bell et al. |
| 5,467,763 A | 11/1995 | McMahon et al. |
| 5,468,250 A | 11/1995 | Paraschac et al. |
| 5,470,308 A | 11/1995 | Edwards et al. |
| 5,470,320 A | 11/1995 | Tiefenbrun et al. |
| 5,478,347 A | 12/1995 | Aranyi |
| 5,480,404 A | 1/1996 | Kammerer et al. |
| 5,482,054 A | 1/1996 | Slater et al. |
| 5,484,451 A | 1/1996 | Akopov et al. |
| 5,489,256 A | 2/1996 | Adair |
| 5,496,347 A | 3/1996 | Hashiguchi et al. |

| | | | | | |
|---|---|---|---|---|---|
| 5,499,990 A | 3/1996 | Schülken et al. | 5,797,928 A | 8/1998 | Kogasaka |
| 5,499,992 A | 3/1996 | Meade et al. | 5,797,939 A | 8/1998 | Yoon |
| 5,501,692 A | 3/1996 | Riza | 5,797,941 A | 8/1998 | Schulze et al. |
| 5,503,616 A | 4/1996 | Jones | 5,803,903 A | 9/1998 | Athas et al. |
| 5,505,686 A | 4/1996 | Willis et al. | 5,808,665 A | 9/1998 | Green |
| 5,507,755 A | 4/1996 | Gresl et al. | 5,810,806 A | 9/1998 | Ritchart et al. |
| 5,511,564 A | 4/1996 | Wilk | 5,810,849 A | 9/1998 | Kontos |
| 5,514,157 A | 5/1996 | Nicholas et al. | 5,810,865 A | 9/1998 | Koscher et al. |
| 5,522,829 A | 6/1996 | Michalos | 5,810,876 A | 9/1998 | Kelleher |
| 5,522,830 A | 6/1996 | Aranyi | 5,810,877 A | 9/1998 | Roth et al. |
| 5,527,321 A | 6/1996 | Hinchliffe | 5,813,976 A | 9/1998 | Filipi et al. |
| 5,540,648 A | 7/1996 | Yoon | 5,814,058 A | 9/1998 | Carlson et al. |
| 5,554,151 A | 9/1996 | Hinchliffe | 5,817,061 A | 10/1998 | Goodwin et al. |
| 5,558,133 A | 9/1996 | Bortoli et al. | 5,817,107 A | 10/1998 | Schaller |
| 5,562,693 A | 10/1996 | Devlin et al. | 5,817,119 A | 10/1998 | Klieman et al. |
| 5,569,243 A | 10/1996 | Kortenbach et al. | 5,819,736 A | 10/1998 | Avny et al. |
| 5,569,298 A | 10/1996 | Schnell | 5,827,281 A | 10/1998 | Levin |
| 5,573,540 A | 11/1996 | Yoon | 5,827,299 A | 10/1998 | Thomason et al. |
| 5,578,030 A | 11/1996 | Levin | 5,830,231 A | 11/1998 | Geiges, Jr. |
| 5,582,611 A | 12/1996 | Tsuruta et al. | 5,833,700 A | 11/1998 | Fogelberg et al. |
| 5,582,617 A | 12/1996 | Klieman et al. | 5,833,703 A | 11/1998 | Manushakian |
| 5,584,845 A | 12/1996 | Hart | 5,843,017 A | 12/1998 | Yoon |
| 5,591,179 A | 1/1997 | Edelstein | 5,849,022 A | 12/1998 | Sakashita et al. |
| 5,593,420 A | 1/1997 | Eubanks, Jr et al. | 5,853,374 A | 12/1998 | Hart et al. |
| 5,595,562 A | 1/1997 | Grier | 5,855,585 A | 1/1999 | Kontos |
| 5,597,378 A | 1/1997 | Jervis | 5,860,913 A | 1/1999 | Yamaya et al. |
| 5,601,573 A | 2/1997 | Fogelberg et al. | 5,860,995 A | 1/1999 | Berkelaar |
| 5,601,588 A | 2/1997 | Tonomura et al. | 5,868,762 A | 2/1999 | Cragg et al. |
| 5,604,531 A | 2/1997 | Iddan et al. | 5,876,411 A | 3/1999 | Kontos |
| 5,607,389 A | 3/1997 | Edwards et al. | 5,882,331 A | 3/1999 | Sasaki |
| 5,607,450 A | 3/1997 | Zvenyatsky et al. | 5,882,344 A | 3/1999 | Stouder, Jr. |
| 5,613,975 A | 3/1997 | Christy | 5,893,846 A | 4/1999 | Bales et al. |
| 5,618,303 A | 4/1997 | Marlow et al. | 5,893,874 A | 4/1999 | Bourque et al. |
| 5,620,415 A | 4/1997 | Lucey et al. | 5,893,875 A | 4/1999 | O'Connor et al. |
| 5,624,399 A | 4/1997 | Ackerman | 5,899,919 A | 5/1999 | Eubanks, Jr. et al. |
| 5,624,431 A | 4/1997 | Gerry et al. | 5,904,702 A | 5/1999 | Ek et al. |
| 5,628,732 A | 5/1997 | Antoon, Jr. et al. | 5,908,420 A | 6/1999 | Parins et al. |
| 5,630,782 A | 5/1997 | Adair | 5,916,147 A | 6/1999 | Boury |
| 5,643,283 A | 7/1997 | Younker | 5,921,993 A | 7/1999 | Yoon |
| 5,643,292 A | 7/1997 | Hart | 5,921,997 A | 7/1999 | Fogelberg et al. |
| 5,643,294 A | 7/1997 | Tovey et al. | 5,922,008 A | 7/1999 | Gimpelson |
| 5,645,083 A | 7/1997 | Essig et al. | 5,925,052 A | 7/1999 | Simmons |
| 5,649,372 A | 7/1997 | Souza | 5,928,255 A | 7/1999 | Meade et al. |
| 5,653,677 A | 8/1997 | Okada et al. | 5,928,266 A | 7/1999 | Kontos |
| 5,653,722 A | 8/1997 | Kieturakis | 5,936,536 A | 8/1999 | Morris |
| 5,662,663 A | 9/1997 | Shallman | 5,944,718 A | 8/1999 | Austin et al. |
| 5,669,875 A | 9/1997 | van Eerdenburg | 5,951,549 A | 9/1999 | Richardson et al. |
| 5,681,324 A | 10/1997 | Kammerer et al. | 5,954,720 A | 9/1999 | Wilson et al. |
| 5,681,330 A | 10/1997 | Hughett et al. | 5,954,731 A | 9/1999 | Yoon |
| 5,685,820 A | 11/1997 | Riek et al. | 5,957,943 A | 9/1999 | Vaitekunas |
| 5,690,656 A | 11/1997 | Cope et al. | 5,957,953 A | 9/1999 | DiPoto et al. |
| 5,690,660 A | 11/1997 | Kauker et al. | 5,971,995 A | 10/1999 | Rousseau |
| 5,695,448 A | 12/1997 | Kimura et al. | 5,976,074 A | 11/1999 | Moriyama |
| 5,695,505 A | 12/1997 | Yoon | 5,976,075 A | 11/1999 | Beane et al. |
| 5,695,511 A | 12/1997 | Cano et al. | 5,976,130 A | 11/1999 | McBrayer et al. |
| 5,700,275 A | 12/1997 | Bell et al. | 5,976,131 A | 11/1999 | Guglielmi et al. |
| 5,709,708 A | 1/1998 | Thal | 5,980,539 A | 11/1999 | Kontos |
| 5,716,326 A | 2/1998 | Dannan | 5,980,556 A | 11/1999 | Giordano et al. |
| 5,730,740 A | 3/1998 | Wales et al. | 5,984,938 A | 11/1999 | Yoon |
| 5,741,278 A | 4/1998 | Stevens | 5,989,182 A | 11/1999 | Hori et al. |
| 5,741,285 A * | 4/1998 | McBrayer et al. ............ 606/170 | 5,993,447 A | 11/1999 | Blewett et al. |
| 5,746,759 A | 5/1998 | Meade et al. | 5,997,555 A | 12/1999 | Kontos |
| 5,749,881 A | 5/1998 | Sackier et al. | 6,001,120 A | 12/1999 | Levin |
| 5,749,889 A | 5/1998 | Bacich et al. | 6,004,330 A | 12/1999 | Middleman et al. |
| 5,752,951 A | 5/1998 | Yanik | 6,007,566 A | 12/1999 | Wenstrom, Jr. |
| 5,766,167 A | 6/1998 | Eggers et al. | 6,010,515 A | 1/2000 | Swain et al. |
| 5,766,170 A | 6/1998 | Eggers | 6,019,770 A | 2/2000 | Christoudias |
| 5,766,205 A | 6/1998 | Zvenyatsky et al. | 6,024,708 A | 2/2000 | Bales et al. |
| 5,769,849 A | 6/1998 | Eggers | 6,024,747 A | 2/2000 | Kontos |
| 5,779,701 A | 7/1998 | McBrayer et al. | 6,027,522 A | 2/2000 | Palmer |
| 5,779,716 A | 7/1998 | Cano et al. | 6,030,365 A | 2/2000 | Laufer |
| 5,779,727 A | 7/1998 | Orejola | 6,033,399 A | 3/2000 | Gines |
| 5,782,859 A | 7/1998 | Nicholas et al. | 6,053,927 A | 4/2000 | Hamas |
| 5,782,866 A | 7/1998 | Wenstrom, Jr. | 6,066,160 A | 5/2000 | Colvin et al. |
| 5,791,022 A | 8/1998 | Bohman | 6,068,603 A | 5/2000 | Suzuki |
| 5,792,113 A | 8/1998 | Kramer et al. | 6,068,629 A | 5/2000 | Haissaguerre et al. |
| 5,792,153 A | 8/1998 | Swain et al. | 6,071,233 A | 6/2000 | Ishikawa et al. |
| 5,792,165 A | 8/1998 | Klieman et al. | 6,074,408 A | 6/2000 | Freeman |
| 5,797,835 A | 8/1998 | Green | 6,086,530 A | 7/2000 | Mack |

| | | | |
|---|---|---|---|
| 6,090,108 A | 7/2000 | McBrayer et al. | |
| 6,096,046 A | 8/2000 | Weiss | |
| 6,110,154 A | 8/2000 | Shimomura et al. | |
| 6,110,183 A | 8/2000 | Cope | |
| 6,117,144 A | 9/2000 | Nobles et al. | |
| 6,117,158 A | 9/2000 | Measamer et al. | |
| 6,139,555 A | 10/2000 | Hart et al. | |
| 6,146,391 A | 11/2000 | Cigaina | |
| 6,149,653 A | 11/2000 | Deslauriers | |
| 6,149,662 A | 11/2000 | Pugliesi et al. | |
| 6,159,200 A | 12/2000 | Verdura et al. | |
| 6,165,184 A | 12/2000 | Verdura et al. | |
| 6,168,570 B1 | 1/2001 | Ferrera | |
| 6,168,605 B1 | 1/2001 | Measamer et al. | |
| 6,170,130 B1 | 1/2001 | Hamilton et al. | |
| 6,179,776 B1 | 1/2001 | Adams et al. | |
| 6,179,837 B1 | 1/2001 | Hooven | |
| 6,190,353 B1 | 2/2001 | Makower et al. | |
| 6,190,384 B1 | 2/2001 | Ouchi | |
| 6,190,399 B1 | 2/2001 | Palmer et al. | |
| 6,203,533 B1 | 3/2001 | Ouchi | |
| 6,206,872 B1 | 3/2001 | Lafond et al. | |
| 6,206,877 B1 | 3/2001 | Kese et al. | |
| 6,214,007 B1 | 4/2001 | Anderson | |
| 6,228,096 B1 | 5/2001 | Marchand | |
| 6,245,079 B1 | 6/2001 | Nobles et al. | |
| 6,258,064 B1 | 7/2001 | Smith et al. | |
| 6,261,242 B1 | 7/2001 | Roberts et al. | |
| 6,264,664 B1 | 7/2001 | Avellanet | |
| 6,270,497 B1 | 8/2001 | Sekino et al. | |
| 6,270,505 B1 | 8/2001 | Yoshida et al. | |
| 6,277,136 B1 | 8/2001 | Bonutti | |
| 6,283,963 B1 | 9/2001 | Regula | |
| 6,293,909 B1 | 9/2001 | Chu et al. | |
| 6,293,952 B1 | 9/2001 | Brosens et al. | |
| 6,296,630 B1 | 10/2001 | Altman et al. | |
| 6,322,578 B1 | 11/2001 | Houle et al. | |
| 6,326,177 B1 | 12/2001 | Schoenbach et al. | |
| 6,328,730 B1 | 12/2001 | Harkrider, Jr. | |
| 6,350,267 B1 | 2/2002 | Stefanchik | |
| 6,352,503 B1 | 3/2002 | Matsui et al. | |
| 6,352,543 B1 | 3/2002 | Cole | |
| 6,355,035 B1 | 3/2002 | Manushakian | |
| 6,371,956 B1 | 4/2002 | Wilson et al. | |
| 6,379,366 B1 | 4/2002 | Fleischman et al. | |
| 6,383,195 B1 | 5/2002 | Richard | |
| 6,383,197 B1 | 5/2002 | Conlon et al. | |
| 6,391,029 B1 | 5/2002 | Hooven et al. | |
| 6,406,440 B1 | 6/2002 | Stefanchik | |
| 6,409,733 B1 | 6/2002 | Conlon et al. | |
| 6,431,500 B1 | 8/2002 | Jacobs et al. | |
| 6,447,511 B1 | 9/2002 | Slater | |
| 6,447,523 B1 | 9/2002 | Middleman et al. | |
| 6,454,783 B1 | 9/2002 | Piskun | |
| 6,454,785 B2 | 9/2002 | De Hoyos Garza | |
| 6,464,701 B1 | 10/2002 | Hooven et al. | |
| 6,475,104 B1 | 11/2002 | Lutz et al. | |
| 6,485,411 B1 | 11/2002 | Konstorum et al. | |
| 6,489,745 B1 | 12/2002 | Koreis | |
| 6,491,626 B1 | 12/2002 | Stone et al. | |
| 6,491,691 B1 | 12/2002 | Morley et al. | |
| 6,494,893 B2 | 12/2002 | Dubrul et al. | |
| 6,503,192 B1 | 1/2003 | Ouchi | |
| 6,506,190 B1 | 1/2003 | Walshe | |
| 6,508,827 B1 | 1/2003 | Manhes | |
| 6,543,456 B1 | 4/2003 | Freeman | |
| 6,551,270 B1 | 4/2003 | Bimbo et al. | |
| 6,554,829 B2 | 4/2003 | Schulze et al. | |
| 6,558,384 B2 | 5/2003 | Mayenberger | |
| 6,562,035 B1 | 5/2003 | Levin | |
| 6,562,052 B2 | 5/2003 | Nobles et al. | |
| 6,569,159 B1 | 5/2003 | Edwards et al. | |
| 6,572,629 B2 | 6/2003 | Kalloo et al. | |
| 6,572,635 B1 | 6/2003 | Bonutti | |
| 6,575,988 B2 | 6/2003 | Rousseau | |
| 6,585,642 B2 | 7/2003 | Christopher | |
| 6,592,559 B1 | 7/2003 | Pakter et al. | |
| 6,592,603 B2 | 7/2003 | Lasner | |
| 6,602,262 B2 | 8/2003 | Griego et al. | |
| 6,605,105 B1 | 8/2003 | Cuschieri et al. | |
| 6,610,072 B1 | 8/2003 | Christy et al. | |
| 6,610,074 B2 | 8/2003 | Santilli | |
| 6,626,919 B1 | 9/2003 | Swanstrom | |
| 6,632,229 B1 | 10/2003 | Yamanouchi | |
| 6,638,286 B1 | 10/2003 | Burbank et al. | |
| 6,652,521 B1 | 11/2003 | Schulze | |
| 6,652,551 B1 | 11/2003 | Heiss | |
| 6,656,194 B1 | 12/2003 | Gannoe et al. | |
| 6,663,641 B1 | 12/2003 | Kovac et al. | |
| 6,666,854 B1 | 12/2003 | Lange | |
| 6,672,338 B1 | 1/2004 | Esashi et al. | |
| 6,673,087 B1 | 1/2004 | Chang et al. | |
| 6,685,628 B2 | 2/2004 | Vu | |
| 6,685,724 B1 | 2/2004 | Haluck | |
| 6,692,445 B2 | 2/2004 | Roberts et al. | |
| 6,692,462 B2 | 2/2004 | Mackenzie et al. | |
| 6,699,180 B2 | 3/2004 | Kobayashi | |
| 6,699,256 B1 | 3/2004 | Logan et al. | |
| 6,699,263 B2 | 3/2004 | Cope | |
| 6,708,066 B2 | 3/2004 | Herbst et al. | |
| 6,716,226 B2 | 4/2004 | Sixto, Jr. et al. | |
| 6,740,030 B2 | 5/2004 | Martone et al. | |
| 6,743,240 B2 | 6/2004 | Smith et al. | |
| 6,749,560 B1 | 6/2004 | Konstorum et al. | |
| 6,749,609 B1 | 6/2004 | Lunsford et al. | |
| 6,752,768 B2 | 6/2004 | Burdorff et al. | |
| 6,752,811 B2 | 6/2004 | Chu et al. | |
| 6,752,822 B2 | 6/2004 | Jespersen | |
| 6,761,685 B2 | 7/2004 | Adams et al. | |
| 6,761,718 B2 | 7/2004 | Madsen | |
| 6,761,722 B2 | 7/2004 | Cole et al. | |
| 6,773,434 B2 | 8/2004 | Ciarrocca | |
| 6,780,151 B2 | 8/2004 | Grabover et al. | |
| 6,780,352 B2 | 8/2004 | Jacobson | |
| 6,783,491 B2 | 8/2004 | Saadat et al. | |
| 6,786,864 B2 | 9/2004 | Matsuura et al. | |
| 6,790,173 B2 | 9/2004 | Saadat et al. | |
| 6,795,728 B2 | 9/2004 | Chornenky et al. | |
| 6,800,056 B2 | 10/2004 | Tartaglia et al. | |
| 6,808,491 B2 | 10/2004 | Kortenbach et al. | |
| 6,824,548 B2 | 11/2004 | Smith et al. | |
| 6,837,847 B2 | 1/2005 | Ewers et al. | |
| 6,843,794 B2 | 1/2005 | Sixto, Jr. et al. | |
| 6,861,250 B1 | 3/2005 | Cole et al. | |
| 6,866,627 B2 | 3/2005 | Nozue | |
| 6,878,106 B1 | 4/2005 | Herrmann | |
| 6,878,110 B2 | 4/2005 | Yang et al. | |
| 6,884,213 B2 | 4/2005 | Raz et al. | |
| 6,887,255 B2 | 5/2005 | Shimm | |
| 6,896,683 B1 | 5/2005 | Gadberry et al. | |
| 6,908,427 B2 | 6/2005 | Fleener et al. | |
| 6,908,476 B2 | 6/2005 | Jud et al. | |
| 6,916,284 B2 | 7/2005 | Moriyama | |
| 6,918,871 B2 | 7/2005 | Schulze | |
| 6,926,725 B2 | 8/2005 | Cooke et al. | |
| 6,932,810 B2 | 8/2005 | Ryan | |
| 6,932,824 B1 | 8/2005 | Roop et al. | |
| 6,932,827 B2 | 8/2005 | Cole | |
| 6,932,834 B2 | 8/2005 | Lizardi et al. | |
| 6,942,613 B2 | 9/2005 | Ewers et al. | |
| 6,945,472 B2 | 9/2005 | Wuttke et al. | |
| 6,945,979 B2 | 9/2005 | Kortenbach et al. | |
| 6,955,683 B2 | 10/2005 | Bonutti | |
| 6,958,035 B2 | 10/2005 | Friedman et al. | |
| 6,960,162 B2 | 11/2005 | Saadat et al. | |
| 6,960,163 B2 | 11/2005 | Ewers et al. | |
| 6,962,587 B2 | 11/2005 | Johnson et al. | |
| 6,964,662 B2 | 11/2005 | Kidooka | |
| 6,966,909 B2 | 11/2005 | Marshall et al. | |
| 6,966,919 B2 | 11/2005 | Sixto, Jr. et al. | |
| 6,967,462 B1 | 11/2005 | Landis | |
| 6,971,988 B2 | 12/2005 | Orban, III | |
| 6,972,017 B2 | 12/2005 | Smith et al. | |
| 6,974,411 B2 | 12/2005 | Belson | |
| 6,976,992 B2 | 12/2005 | Sachatello et al. | |
| 6,984,203 B2 | 1/2006 | Tartaglia et al. | |
| 6,984,205 B2 | 1/2006 | Gazdzinski | |
| 6,986,774 B2 | 1/2006 | Middleman et al. | |

| Patent No. | Date | Inventor |
|---|---|---|
| 6,988,987 B2 | 1/2006 | Ishikawa et al. |
| 6,991,627 B2 | 1/2006 | Madhani et al. |
| 6,994,708 B2 | 2/2006 | Manzo |
| 6,997,931 B2 | 2/2006 | Sauer et al. |
| 7,000,818 B2 | 2/2006 | Shelton, IV et al. |
| 7,008,375 B2 | 3/2006 | Weisel |
| 7,009,634 B2 | 3/2006 | Iddan et al. |
| 7,010,340 B2 | 3/2006 | Scarantino et al. |
| 7,020,531 B1 | 3/2006 | Colliou et al. |
| 7,025,580 B2 | 4/2006 | Heagy et al. |
| 7,029,435 B2 | 4/2006 | Nakao |
| 7,029,438 B2 | 4/2006 | Morin et al. |
| 7,037,290 B2 | 5/2006 | Gardeski et al. |
| 7,041,052 B2 | 5/2006 | Saadat et al. |
| 7,052,489 B2 | 5/2006 | Griego et al. |
| 7,060,024 B2 | 6/2006 | Long et al. |
| 7,060,025 B2 | 6/2006 | Long et al. |
| 7,063,697 B2 | 6/2006 | Slater |
| 7,063,715 B2 | 6/2006 | Onuki et al. |
| 7,066,879 B2 | 6/2006 | Fowler et al. |
| 7,066,936 B2 | 6/2006 | Ryan |
| 7,070,602 B2 | 7/2006 | Smith et al. |
| 7,076,305 B2 | 7/2006 | Imran et al. |
| 7,083,629 B2 | 8/2006 | Weller et al. |
| 7,087,071 B2 | 8/2006 | Nicholas et al. |
| 7,090,673 B2 | 8/2006 | Dycus et al. |
| 7,090,685 B2 | 8/2006 | Kortenbach et al. |
| 7,093,518 B2 | 8/2006 | Gmeilbauer |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,105,000 B2 | 9/2006 | McBrayer |
| 7,105,005 B2 | 9/2006 | Blake |
| 7,108,703 B2 | 9/2006 | Danitz et al. |
| 7,112,208 B2 | 9/2006 | Morris et al. |
| 7,118,531 B2 | 10/2006 | Krill |
| 7,118,578 B2 | 10/2006 | West, Jr. et al. |
| 7,118,587 B2 | 10/2006 | Dycus et al. |
| 7,128,708 B2 | 10/2006 | Saadat et al. |
| RE39,415 E | 11/2006 | Bales et al. |
| 7,131,978 B2 | 11/2006 | Sancoff et al. |
| 7,131,979 B2 | 11/2006 | DiCarlo et al. |
| 7,131,980 B1 | 11/2006 | Field et al. |
| 7,137,980 B2 | 11/2006 | Buysse et al. |
| 7,137,981 B2 | 11/2006 | Long |
| 7,146,984 B2 | 12/2006 | Stack et al. |
| 7,147,650 B2 | 12/2006 | Lee |
| 7,153,321 B2 | 12/2006 | Andrews |
| 7,163,525 B2 | 1/2007 | Franer |
| 7,172,714 B2 | 2/2007 | Jacobson |
| 7,179,254 B2 | 2/2007 | Pendekanti et al. |
| 7,195,612 B2 | 3/2007 | Van Sloten et al. |
| 7,195,631 B2 | 3/2007 | Dumbauld |
| 7,208,005 B2 | 4/2007 | Frecker et al. |
| 7,211,092 B2 | 5/2007 | Hughett |
| 7,223,272 B2 | 5/2007 | Francere et al. |
| 7,232,414 B2 | 6/2007 | Gonzalez |
| 7,232,445 B2 | 6/2007 | Kortenbach et al. |
| 7,241,290 B2 | 7/2007 | Doyle et al. |
| 7,244,228 B2 | 7/2007 | Lubowski |
| 7,252,660 B2 | 8/2007 | Kunz |
| 7,270,663 B2 | 9/2007 | Nakao |
| 7,294,139 B1 | 11/2007 | Gengler |
| 7,301,250 B2 | 11/2007 | Cassel |
| 7,306,597 B2 | 12/2007 | Manzo |
| 7,318,802 B2 | 1/2008 | Suzuki et al. |
| 7,320,695 B2 | 1/2008 | Carroll |
| 7,322,934 B2 | 1/2008 | Miyake et al. |
| 7,329,257 B2 | 2/2008 | Kanehira et al. |
| 7,329,383 B2 | 2/2008 | Stinson |
| 7,344,536 B1 | 3/2008 | Lunsford et al. |
| 7,364,582 B2 | 4/2008 | Lee |
| 7,371,215 B2 | 5/2008 | Colliou et al. |
| 7,381,216 B2 | 6/2008 | Buzzard et al. |
| 7,393,322 B2 | 7/2008 | Wenchell |
| 7,402,162 B2 | 7/2008 | Ouchi |
| 7,404,791 B2 | 7/2008 | Linares et al. |
| 7,416,554 B2 | 8/2008 | Lam et al. |
| 7,422,590 B2 | 9/2008 | Kupferschmid et al. |
| 7,455,208 B2 | 11/2008 | Wales et al. |
| 7,488,295 B2 | 2/2009 | Burbank et al. |
| 7,497,867 B2 | 3/2009 | Lasner et al. |
| 7,507,200 B2 | 3/2009 | Okada |
| 7,524,281 B2 | 4/2009 | Chu et al. |
| 7,534,228 B2 | 5/2009 | Williams |
| 7,544,203 B2 | 6/2009 | Chin et al. |
| 7,548,040 B2 | 6/2009 | Lee et al. |
| 7,549,564 B2 | 6/2009 | Boudreaux |
| 7,553,278 B2 | 6/2009 | Kucklick |
| 7,553,298 B2 | 6/2009 | Hunt et al. |
| 7,559,887 B2 | 7/2009 | Dannan |
| 7,561,916 B2 | 7/2009 | Hunt et al. |
| 7,566,334 B2 | 7/2009 | Christian et al. |
| 7,575,144 B2 | 8/2009 | Ortiz et al. |
| 7,579,550 B2 | 8/2009 | Dayton et al. |
| 7,582,096 B2 | 9/2009 | Gellman et al. |
| 7,588,177 B2 | 9/2009 | Racenet |
| 7,635,373 B2 | 12/2009 | Ortiz |
| 7,651,483 B2 | 1/2010 | Byrum et al. |
| 7,651,509 B2 | 1/2010 | Bojarski et al. |
| 7,654,431 B2 | 2/2010 | Hueil et al. |
| 7,662,089 B2 | 2/2010 | Okada et al. |
| 7,666,180 B2 | 2/2010 | Holsten et al. |
| 7,713,270 B2 | 5/2010 | Suzuki |
| 7,736,374 B2 | 6/2010 | Vaughan et al. |
| 7,762,998 B2 | 7/2010 | Birk et al. |
| 7,780,683 B2 | 8/2010 | Roue et al. |
| 7,794,475 B2 | 9/2010 | Hess et al. |
| 7,850,660 B2 | 12/2010 | Uth et al. |
| 7,862,546 B2 | 1/2011 | Conlon et al. |
| 7,918,869 B2 | 4/2011 | Saadat et al. |
| 2001/0049497 A1 | 12/2001 | Kalloo et al. |
| 2002/0022857 A1 | 2/2002 | Goldsteen et al. |
| 2002/0023353 A1 | 2/2002 | Ting-Kung |
| 2002/0042562 A1 | 4/2002 | Meron et al. |
| 2002/0049439 A1 | 4/2002 | Mulier et al. |
| 2002/0068945 A1 | 6/2002 | Sixto, Jr. et al. |
| 2002/0078967 A1 | 6/2002 | Sixto, Jr. et al. |
| 2002/0082516 A1 | 6/2002 | Stefanchik |
| 2002/0095164 A1 | 7/2002 | Andreas et al. |
| 2002/0107530 A1 | 8/2002 | Sauer et al. |
| 2002/0133115 A1 | 9/2002 | Gordon et al. |
| 2002/0138086 A1 | 9/2002 | Sixto, Jr. et al. |
| 2002/0147456 A1 | 10/2002 | Diduch et al. |
| 2002/0183591 A1 | 12/2002 | Matsuura et al. |
| 2003/0036679 A1 | 2/2003 | Kortenbach et al. |
| 2003/0069602 A1 | 4/2003 | Jacobs et al. |
| 2003/0114732 A1 | 6/2003 | Webler et al. |
| 2003/0130564 A1 | 7/2003 | Martone et al. |
| 2003/0130656 A1 | 7/2003 | Levin |
| 2003/0158521 A1 | 8/2003 | Ameri |
| 2003/0167062 A1 | 9/2003 | Gambale et al. |
| 2003/0171651 A1 | 9/2003 | Page et al. |
| 2003/0176880 A1 | 9/2003 | Long et al. |
| 2003/0216611 A1 | 11/2003 | Vu |
| 2003/0216615 A1 | 11/2003 | Ouchi |
| 2003/0220545 A1 | 11/2003 | Ouchi |
| 2003/0225312 A1 | 12/2003 | Suzuki et al. |
| 2003/0225332 A1 | 12/2003 | Okada et al. |
| 2003/0229269 A1 | 12/2003 | Humphrey |
| 2003/0229371 A1 | 12/2003 | Whitworth |
| 2003/0236549 A1 | 12/2003 | Bonadio et al. |
| 2004/0098007 A1 | 5/2004 | Heiss |
| 2004/0101456 A1 | 5/2004 | Kuroshima et al. |
| 2004/0116948 A1 | 6/2004 | Sixto, Jr. et al. |
| 2004/0133089 A1 | 7/2004 | Kilcoyne et al. |
| 2004/0136779 A1 | 7/2004 | Bhaskar |
| 2004/0138525 A1 | 7/2004 | Saadat et al. |
| 2004/0138529 A1 | 7/2004 | Wiltshire et al. |
| 2004/0138587 A1 | 7/2004 | Lyons, IV |
| 2004/0186350 A1 | 9/2004 | Brenneman et al. |
| 2004/0193009 A1 | 9/2004 | Jaffe et al. |
| 2004/0193146 A1 | 9/2004 | Lee et al. |
| 2004/0193186 A1 | 9/2004 | Kortenbach et al. |
| 2004/0193188 A1 | 9/2004 | Francese |
| 2004/0193189 A1 | 9/2004 | Kortenbach et al. |
| 2004/0193200 A1 | 9/2004 | Dworschak et al. |
| 2004/0199052 A1 | 10/2004 | Banik et al. |

| | | | | | | |
|---|---|---|---|---|---|---|
| 2004/0210245 A1 | 10/2004 | Erickson et al. | | 2006/0025781 A1 | 2/2006 | Young et al. |
| 2004/0215058 A1 | 10/2004 | Zirps et al. | | 2006/0025819 A1 | 2/2006 | Nobis et al. |
| 2004/0225183 A1 | 11/2004 | Michlitsch et al. | | 2006/0036267 A1 | 2/2006 | Saadat et al. |
| 2004/0225186 A1 | 11/2004 | Horne, Jr. et al. | | 2006/0041188 A1 | 2/2006 | Dirusso et al. |
| 2004/0230095 A1 | 11/2004 | Stefanchik et al. | | 2006/0058582 A1 | 3/2006 | Maahs et al. |
| 2004/0230096 A1 | 11/2004 | Stefanchik et al. | | 2006/0058776 A1 | 3/2006 | Bilsbury |
| 2004/0230097 A1 | 11/2004 | Stefanchik et al. | | 2006/0069396 A1 | 3/2006 | Meade et al. |
| 2004/0230161 A1 | 11/2004 | Zeiner | | 2006/0079890 A1 | 4/2006 | Guerra |
| 2004/0249246 A1 | 12/2004 | Campos | | 2006/0089528 A1 | 4/2006 | Tartaglia et al. |
| 2004/0249367 A1 | 12/2004 | Saadat et al. | | 2006/0095060 A1 | 5/2006 | Mayenberger et al. |
| 2004/0249394 A1 | 12/2004 | Morris et al. | | 2006/0106423 A1 | 5/2006 | Weisel et al. |
| 2005/0033277 A1 | 2/2005 | Clague et al. | | 2006/0111209 A1 | 5/2006 | Hinman et al. |
| 2005/0033319 A1 | 2/2005 | Gambale et al. | | 2006/0111210 A1 | 5/2006 | Hinman et al. |
| 2005/0033333 A1 | 2/2005 | Smith et al. | | 2006/0111704 A1 | 5/2006 | Brenneman et al. |
| 2005/0043690 A1 | 2/2005 | Todd | | 2006/0129166 A1 | 6/2006 | Lavelle |
| 2005/0049616 A1 | 3/2005 | Rivera et al. | | 2006/0135962 A1 | 6/2006 | Kick et al. |
| 2005/0065397 A1 | 3/2005 | Saadat et al. | | 2006/0135971 A1 | 6/2006 | Swanstrom et al. |
| 2005/0065517 A1 | 3/2005 | Chin | | 2006/0135984 A1 | 6/2006 | Kramer et al. |
| 2005/0070754 A1 | 3/2005 | Nobis et al. | | 2006/0142644 A1 | 6/2006 | Mulac et al. |
| 2005/0070763 A1 | 3/2005 | Nobis et al. | | 2006/0142652 A1 | 6/2006 | Keenan |
| 2005/0070764 A1 | 3/2005 | Nobis et al. | | 2006/0142790 A1 | 6/2006 | Gertner |
| 2005/0080413 A1 | 4/2005 | Canady | | 2006/0142798 A1 | 6/2006 | Holman et al. |
| 2005/0085693 A1 | 4/2005 | Belson et al. | | 2006/0149132 A1 | 7/2006 | Iddan |
| 2005/0085832 A1 | 4/2005 | Sancoff et al. | | 2006/0149135 A1 | 7/2006 | Paz |
| 2005/0090837 A1 | 4/2005 | Sixto, Jr. et al. | | 2006/0161190 A1 | 7/2006 | Gadberry et al. |
| 2005/0090838 A1 | 4/2005 | Sixto, Jr. et al. | | 2006/0167416 A1 | 7/2006 | Mathis et al. |
| 2005/0101837 A1 | 5/2005 | Kalloo et al. | | 2006/0167482 A1 | 7/2006 | Swain et al. |
| 2005/0101838 A1 | 5/2005 | Camillocci et al. | | 2006/0178560 A1 | 8/2006 | Saadat et al. |
| 2005/0107663 A1 | 5/2005 | Saadat et al. | | 2006/0183975 A1 | 8/2006 | Saadat et al. |
| 2005/0107664 A1 | 5/2005 | Kalloo et al. | | 2006/0184161 A1 | 8/2006 | Maahs et al. |
| 2005/0110881 A1 | 5/2005 | Glukhovsky et al. | | 2006/0189844 A1 | 8/2006 | Tien |
| 2005/0113847 A1 | 5/2005 | Gadberry et al. | | 2006/0189845 A1 | 8/2006 | Maahs et al. |
| 2005/0124855 A1 | 6/2005 | Jaffe et al. | | 2006/0190027 A1 | 8/2006 | Downey |
| 2005/0125010 A1 | 6/2005 | Smith et al. | | 2006/0195084 A1 | 8/2006 | Slater |
| 2005/0131279 A1 | 6/2005 | Boulais et al. | | 2006/0200005 A1 | 9/2006 | Bjork et al. |
| 2005/0131457 A1 | 6/2005 | Douglas et al. | | 2006/0200169 A1 | 9/2006 | Sniffin |
| 2005/0137454 A1 | 6/2005 | Saadat et al. | | 2006/0200170 A1 | 9/2006 | Aranyi |
| 2005/0143690 A1 | 6/2005 | High | | 2006/0200199 A1 | 9/2006 | Bonutti et al. |
| 2005/0143774 A1 | 6/2005 | Polo | | 2006/0217697 A1 | 9/2006 | Lau et al. |
| 2005/0149087 A1 | 7/2005 | Ahlberg et al. | | 2006/0217742 A1 | 9/2006 | Messerly et al. |
| 2005/0149096 A1 | 7/2005 | Hilal et al. | | 2006/0217743 A1 | 9/2006 | Messerly et al. |
| 2005/0159648 A1 | 7/2005 | Freed | | 2006/0229639 A1 | 10/2006 | Whitfield |
| 2005/0165272 A1 | 7/2005 | Okada et al. | | 2006/0229640 A1 | 10/2006 | Whitfield |
| 2005/0165378 A1 | 7/2005 | Heinrich et al. | | 2006/0237022 A1 | 10/2006 | Chen et al. |
| 2005/0165411 A1 | 7/2005 | Orban, III | | 2006/0237023 A1 | 10/2006 | Cox et al. |
| 2005/0165429 A1 | 7/2005 | Douglas et al. | | 2006/0241570 A1 | 10/2006 | Wilk |
| 2005/0182429 A1 | 8/2005 | Yamanouchi | | 2006/0247673 A1 | 11/2006 | Voegele et al. |
| 2005/0192598 A1 | 9/2005 | Johnson et al. | | 2006/0253004 A1 | 11/2006 | Frisch et al. |
| 2005/0192602 A1 | 9/2005 | Manzo | | 2006/0253039 A1 | 11/2006 | McKenna et al. |
| 2005/0192654 A1 | 9/2005 | Chanduszko et al. | | 2006/0258907 A1 | 11/2006 | Stefanchik et al. |
| 2005/0209624 A1 | 9/2005 | Vijay | | 2006/0258908 A1 | 11/2006 | Stefanchik et al. |
| 2005/0215858 A1 | 9/2005 | Vail, III | | 2006/0258910 A1 | 11/2006 | Stefanchik et al. |
| 2005/0216050 A1 | 9/2005 | Sepetka et al. | | 2006/0258954 A1 | 11/2006 | Timberlake et al. |
| 2005/0228406 A1 | 10/2005 | Bose | | 2006/0258955 A1 | 11/2006 | Hoffman et al. |
| 2005/0234297 A1 | 10/2005 | Devierre et al. | | 2006/0259010 A1 | 11/2006 | Stefanchik et al. |
| 2005/0250990 A1 | 11/2005 | Le et al. | | 2006/0264752 A1 | 11/2006 | Rubinsky et al. |
| 2005/0251176 A1 | 11/2005 | Swanstrom et al. | | 2006/0264930 A1 | 11/2006 | Nishimura |
| 2005/0261674 A1 | 11/2005 | Nobis et al. | | 2006/0270902 A1 | 11/2006 | Igarashi et al. |
| 2005/0267492 A1 | 12/2005 | Poncet et al. | | 2006/0271102 A1 | 11/2006 | Bosshard et al. |
| 2005/0272975 A1 | 12/2005 | McWeeney et al. | | 2006/0276835 A1 | 12/2006 | Uchida |
| 2005/0272977 A1 | 12/2005 | Saadat et al. | | 2006/0281970 A1 | 12/2006 | Stokes et al. |
| 2005/0273084 A1 | 12/2005 | Hinman et al. | | 2006/0285732 A1 | 12/2006 | Horn et al. |
| 2005/0277945 A1 | 12/2005 | Saadat et al. | | 2006/0287644 A1 | 12/2006 | Inganas et al. |
| 2005/0277951 A1 | 12/2005 | Smith et al. | | 2006/0287666 A1 | 12/2006 | Saadat et al. |
| 2005/0277952 A1 | 12/2005 | Arp et al. | | 2006/0293626 A1 | 12/2006 | Byrum et al. |
| 2005/0277954 A1 | 12/2005 | Smith et al. | | 2007/0002135 A1 | 1/2007 | Glukhovsky |
| 2005/0277955 A1 | 12/2005 | Palmer et al. | | 2007/0005019 A1 | 1/2007 | Okishige |
| 2005/0277956 A1 | 12/2005 | Francese et al. | | 2007/0015965 A1 | 1/2007 | Cox et al. |
| 2005/0277957 A1 | 12/2005 | Kuhns et al. | | 2007/0016255 A1 | 1/2007 | Korb et al. |
| 2005/0283118 A1 | 12/2005 | Uth et al. | | 2007/0032700 A1 | 2/2007 | Fowler et al. |
| 2005/0283119 A1 | 12/2005 | Uth et al. | | 2007/0032701 A1 | 2/2007 | Fowler et al. |
| 2005/0288555 A1 | 12/2005 | Binmoeller | | 2007/0043345 A1 | 2/2007 | Davalos et al. |
| 2006/0004406 A1 | 1/2006 | Wehrstein et al. | | 2007/0049800 A1 | 3/2007 | Boulais |
| 2006/0004409 A1 | 1/2006 | Nobis et al. | | 2007/0051375 A1 | 3/2007 | Milliman |
| 2006/0004410 A1 | 1/2006 | Nobis et al. | | 2007/0060880 A1 | 3/2007 | Gregorich et al. |
| 2006/0015009 A1 | 1/2006 | Jaffe et al. | | 2007/0073102 A1 | 3/2007 | Matsuno et al. |
| 2006/0020167 A1 | 1/2006 | Sitzmann | | 2007/0079924 A1 | 4/2007 | Saadat et al. |
| 2006/0020247 A1 | 1/2006 | Kagan et al. | | 2007/0088370 A1 | 4/2007 | Kahle et al. |
| 2006/0025654 A1 | 2/2006 | Suzuki et al. | | 2007/0100375 A1 | 5/2007 | Mikkaichi et al. |

| | | | | | | |
|---|---|---|---|---|---|---|
| 2007/0100376 A1 | 5/2007 | Mikkaichi et al. | | 2008/0269783 A1 | 10/2008 | Griffith |
| 2007/0106118 A1 | 5/2007 | Moriyama | | 2008/0275474 A1 | 11/2008 | Martin et al. |
| 2007/0112251 A1 | 5/2007 | Nakhuda | | 2008/0275475 A1 | 11/2008 | Schwemberger et al. |
| 2007/0112331 A1 | 5/2007 | Weber et al. | | 2008/0300547 A1 | 12/2008 | Bakos |
| 2007/0112342 A1 | 5/2007 | Pearson et al. | | 2008/0309758 A1 | 12/2008 | Karasawa et al. |
| 2007/0112383 A1 | 5/2007 | Conlon et al. | | 2008/0312496 A1 | 12/2008 | Zwolinski |
| 2007/0112384 A1 | 5/2007 | Conlon et al. | | 2008/0312499 A1 | 12/2008 | Handa et al. |
| 2007/0112385 A1 | 5/2007 | Conlon | | 2008/0312500 A1 | 12/2008 | Asada et al. |
| 2007/0112425 A1 | 5/2007 | Schaller et al. | | 2008/0312506 A1 | 12/2008 | Spivey et al. |
| 2007/0118115 A1 | 5/2007 | Artale et al. | | 2008/0319436 A1 | 12/2008 | Daniel et al. |
| 2007/0123840 A1 | 5/2007 | Cox | | 2008/0319439 A1 | 12/2008 | Ootsubu |
| 2007/0129719 A1 | 6/2007 | Kendale et al. | | 2009/0054728 A1 | 2/2009 | Trusty |
| 2007/0135709 A1 | 6/2007 | Rioux et al. | | 2009/0062788 A1 | 3/2009 | Long et al. |
| 2007/0156127 A1 | 7/2007 | Rioux et al. | | 2009/0062792 A1 | 3/2009 | Vakharia et al. |
| 2007/0161855 A1 | 7/2007 | Mikkaichi et al. | | 2009/0062795 A1 | 3/2009 | Vakharia et al. |
| 2007/0173869 A1 | 7/2007 | Gannoe et al. | | 2009/0076499 A1 | 3/2009 | Azure |
| 2007/0173870 A2 | 7/2007 | Zacharias | | 2009/0082776 A1 | 3/2009 | Cresina |
| 2007/0173872 A1 | 7/2007 | Neuenfeldt | | 2009/0082779 A1 | 3/2009 | Nakao |
| 2007/0179525 A1 | 8/2007 | Frecker et al. | | 2009/0112059 A1 | 4/2009 | Nobis |
| 2007/0179530 A1 | 8/2007 | Tieu et al. | | 2009/0112062 A1 | 4/2009 | Bakos |
| 2007/0197865 A1 | 8/2007 | Miyake et al. | | 2009/0112063 A1 | 4/2009 | Bakos et al. |
| 2007/0203487 A1 | 8/2007 | Sugita | | 2009/0131751 A1 | 5/2009 | Spivey et al. |
| 2007/0208364 A1 | 9/2007 | Smith et al. | | 2009/0131932 A1 | 5/2009 | Vakharia et al. |
| 2007/0213754 A1 | 9/2007 | Mikkaichi et al. | | 2009/0131933 A1 | 5/2009 | Ghabrial et al. |
| 2007/0225554 A1 | 9/2007 | Maseda et al. | | 2009/0143639 A1 | 6/2009 | Stark |
| 2007/0233040 A1 | 10/2007 | Macnamara et al. | | 2009/0143794 A1 | 6/2009 | Conlon et al. |
| 2007/0244358 A1 | 10/2007 | Lee | | 2009/0149710 A1 | 6/2009 | Stefanchik et al. |
| 2007/0250057 A1 | 10/2007 | Nobis et al. | | 2009/0177031 A1 | 7/2009 | Surti et al. |
| 2007/0255096 A1 | 11/2007 | Stefanchik et al. | | 2009/0177219 A1 | 7/2009 | Conlon |
| 2007/0255100 A1 | 11/2007 | Barlow et al. | | 2009/0182332 A1 | 7/2009 | Long et al. |
| 2007/0255273 A1 | 11/2007 | Fernandez et al. | | 2009/0192344 A1 | 7/2009 | Bakos et al. |
| 2007/0255303 A1 | 11/2007 | Bakos et al. | | 2009/0198231 A1 | 8/2009 | Esser et al. |
| 2007/0255306 A1 | 11/2007 | Conlon et al. | | 2009/0227828 A1 | 9/2009 | Swain et al. |
| 2007/0260112 A1 | 11/2007 | Rahmani | | 2009/0248055 A1 | 10/2009 | Spivey et al. |
| 2007/0260117 A1 | 11/2007 | Zwolinski et al. | | 2009/0281559 A1 | 11/2009 | Swain et al. |
| 2007/0260121 A1 | 11/2007 | Bakos et al. | | 2009/0287236 A1 | 11/2009 | Bakos et al. |
| 2007/0260273 A1 | 11/2007 | Cropper et al. | | 2009/0292164 A1 | 11/2009 | Yamatani |
| 2007/0270629 A1 | 11/2007 | Charles | | 2009/0299135 A1 | 12/2009 | Spivey |
| 2007/0270889 A1 | 11/2007 | Conlon et al. | | 2009/0299143 A1 | 12/2009 | Conlon et al. |
| 2007/0270895 A1 | 11/2007 | Nobis et al. | | 2009/0299362 A1 | 12/2009 | Long et al. |
| 2007/0270907 A1 | 11/2007 | Stokes et al. | | 2009/0299385 A1 | 12/2009 | Stefanchik et al. |
| 2007/0282371 A1 | 12/2007 | Lee et al. | | 2009/0299406 A1 | 12/2009 | Swain et al. |
| 2008/0004650 A1 | 1/2008 | George | | 2009/0299409 A1 | 12/2009 | Coe et al. |
| 2008/0015409 A1 | 1/2008 | Barlow et al. | | 2009/0306658 A1 | 12/2009 | Nobis et al. |
| 2008/0015552 A1 | 1/2008 | Doyle et al. | | 2009/0306683 A1 | 12/2009 | Zwolinski et al. |
| 2008/0027387 A1 | 1/2008 | Grabinsky | | 2009/0322864 A1 | 12/2009 | Karasawa et al. |
| 2008/0033451 A1 | 2/2008 | Rieber et al. | | 2009/0326561 A1 | 12/2009 | Carroll, II et al. |
| 2008/0051629 A1 | 2/2008 | Sugiyama et al. | | 2010/0010294 A1 | 1/2010 | Conlon et al. |
| 2008/0051735 A1 | 2/2008 | Measamer et al. | | 2010/0010298 A1 | 1/2010 | Bakos et al. |
| 2008/0058586 A1 | 3/2008 | Karpiel | | 2010/0010299 A1 | 1/2010 | Bakos et al. |
| 2008/0065169 A1 | 3/2008 | Colliou et al. | | 2010/0010303 A1 | 1/2010 | Bakos |
| 2008/0086172 A1 | 4/2008 | Martin et al. | | 2010/0010510 A1 | 1/2010 | Stefanchik |
| 2008/0097472 A1 | 4/2008 | Agmon et al. | | 2010/0010511 A1 | 1/2010 | Harris et al. |
| 2008/0097483 A1 | 4/2008 | Ortiz et al. | | 2010/0023032 A1 | 1/2010 | Granja Filho |
| 2008/0103527 A1 | 5/2008 | Martin et al. | | 2010/0042045 A1 | 2/2010 | Spivey |
| 2008/0114384 A1 | 5/2008 | Chang et al. | | 2010/0048990 A1 | 2/2010 | Bakos |
| 2008/0119870 A1 | 5/2008 | Williams | | 2010/0049190 A1 | 2/2010 | Long et al. |
| 2008/0125796 A1 | 5/2008 | Graham | | 2010/0049223 A1 | 2/2010 | Granja Filho |
| 2008/0132892 A1 | 6/2008 | Lunsford et al. | | 2010/0056861 A1 | 3/2010 | Spivey |
| 2008/0139882 A1 | 6/2008 | Fujimori | | 2010/0056862 A1 | 3/2010 | Bakos |
| 2008/0147113 A1 | 6/2008 | Nobis et al. | | 2010/0057085 A1 | 3/2010 | Holcomb et al. |
| 2008/0171907 A1 | 7/2008 | Long et al. | | 2010/0057108 A1 | 3/2010 | Spivey et al. |
| 2008/0200755 A1 | 8/2008 | Bakos | | 2010/0063538 A1 | 3/2010 | Spivey et al. |
| 2008/0200762 A1 | 8/2008 | Stokes et al. | | 2010/0076451 A1 | 3/2010 | Zwolinski et al. |
| 2008/0200911 A1 | 8/2008 | Long | | 2010/0081877 A1 | 4/2010 | Vakharia |
| 2008/0200912 A1 | 8/2008 | Long | | 2010/0087813 A1 | 4/2010 | Long |
| 2008/0200933 A1 | 8/2008 | Bakos et al. | | 2010/0113872 A1 | 5/2010 | Asada et al. |
| 2008/0200934 A1 | 8/2008 | Fox | | 2010/0121362 A1 | 5/2010 | Clague et al. |
| 2008/0208213 A1 | 8/2008 | Benjamin et al. | | 2010/0130817 A1 | 5/2010 | Conlon |
| 2008/0221587 A1 | 9/2008 | Schwartz | | 2010/0130975 A1 | 5/2010 | Long |
| 2008/0221619 A1 | 9/2008 | Spivey et al. | | 2010/0131005 A1 | 5/2010 | Conlon |
| 2008/0228213 A1 | 9/2008 | Blakeney et al. | | 2010/0152539 A1 | 6/2010 | Ghabrial et al. |
| 2008/0230972 A1 | 9/2008 | Ganley | | 2010/0152609 A1 | 6/2010 | Zwolinski et al. |
| 2008/0234696 A1 | 9/2008 | Taylor et al. | | 2010/0152746 A1 | 6/2010 | Ceniccola et al. |
| 2008/0243106 A1 | 10/2008 | Coe et al. | | 2010/0179510 A1 | 7/2010 | Fox et al. |
| 2008/0243148 A1 | 10/2008 | Mikkaichi et al. | | 2010/0179530 A1 | 7/2010 | Long et al. |
| 2008/0243176 A1 | 10/2008 | Weitzner et al. | | 2010/0191050 A1 | 7/2010 | Zwolinski |
| 2008/0262540 A1 | 10/2008 | Bangera et al. | | 2010/0191267 A1 | 7/2010 | Fox |
| 2008/0269782 A1 | 10/2008 | Stefanchik et al. | | 2010/0198005 A1 | 8/2010 | Fox |

| | | | |
|---|---|---|---|
| 2010/0198149 A1 | 8/2010 | Fox | |
| 2010/0198248 A1 | 8/2010 | Vakharia | |
| 2010/0249700 A1 | 9/2010 | Spivey | |
| 2010/0286791 A1 | 11/2010 | Goldsmith | |
| 2010/0298642 A1 | 11/2010 | Trusty et al. | |
| 2010/0331622 A2 | 12/2010 | Conlon | |
| 2010/0331774 A2 | 12/2010 | Spivey | |
| 2011/0093009 A1 | 4/2011 | Fox | |
| 2011/0098694 A1 | 4/2011 | Long | |
| 2011/0098704 A1 | 4/2011 | Long et al. | |
| 2011/0105850 A1 | 5/2011 | Voegele et al. | |
| 2011/0112434 A1 | 5/2011 | Ghabrial et al. | |
| 2011/0115891 A1 | 5/2011 | Trusty | |
| 2011/0124964 A1 | 5/2011 | Nobis | |

FOREIGN PATENT DOCUMENTS

| | | | |
|---|---|---|---|
| DE | 4323585 A1 | 1/1995 | |
| DE | 19757056 B4 | 8/2008 | |
| DE | 102006027873 B4 | 10/2009 | |
| EP | 0086338 A1 | 8/1983 | |
| EP | 0286415 A2 | 10/1988 | |
| EP | 0589454 A2 | 3/1994 | |
| EP | 0464479 B1 | 3/1995 | |
| EP | 0529675 B1 | 2/1996 | |
| EP | 0724863 B1 | 7/1999 | |
| EP | 0760629 B1 | 11/1999 | |
| EP | 0818974 B1 | 7/2001 | |
| EP | 0947166 B1 | 5/2003 | |
| EP | 0836832 B1 | 12/2003 | |
| EP | 1402837 A1 | 3/2004 | |
| EP | 0744918 B1 | 4/2004 | |
| EP | 0931515 B1 | 8/2004 | |
| EP | 1411843 B1 | 10/2004 | |
| EP | 1150614 B1 | 11/2004 | |
| EP | 1477104 A1 | 11/2004 | |
| EP | 1481642 A1 | 12/2004 | |
| EP | 1493391 A1 | 1/2005 | |
| EP | 0848598 B1 | 2/2005 | |
| EP | 1281360 B1 | 3/2005 | |
| EP | 1568330 A1 | 8/2005 | |
| EP | 1452143 B1 | 9/2005 | |
| EP | 1616527 A2 | 1/2006 | |
| EP | 1006888 B1 | 3/2006 | |
| EP | 1629764 A1 | 3/2006 | |
| EP | 1013229 B1 | 6/2006 | |
| EP | 1721561 A1 | 11/2006 | |
| EP | 1153578 B1 | 3/2007 | |
| EP | 1334696 B1 | 3/2007 | |
| EP | 1769766 A1 | 4/2007 | |
| EP | 1836971 A2 | 9/2007 | |
| EP | 1836980 A1 | 9/2007 | |
| EP | 1854421 A2 | 11/2007 | |
| EP | 1857061 A1 | 11/2007 | |
| EP | 1875876 A1 | 1/2008 | |
| EP | 1891881 A1 | 2/2008 | |
| EP | 1902663 A1 | 3/2008 | |
| EP | 1477106 B1 | 6/2008 | |
| EP | 1949844 A1 | 7/2008 | |
| EP | 1518499 B1 | 8/2008 | |
| EP | 1709918 B1 | 10/2008 | |
| EP | 1985226 A2 | 10/2008 | |
| EP | 1994904 A1 | 11/2008 | |
| EP | 1707130 B1 | 12/2008 | |
| EP | 1769749 B1 | 11/2009 | |
| FR | 2731610 A1 | 9/1996 | |
| GB | 2403909 A | 1/2005 | |
| GB | 2443261 A | 4/2008 | |
| JP | 56-46674 | 4/1981 | |
| JP | 8-29699 A | 2/1996 | |
| JP | 2002-369791 A | 12/2002 | |
| JP | 2003-088494 A | 3/2003 | |
| JP | 2003-235852 A | 8/2003 | |
| JP | 2004-33525 A | 2/2004 | |
| JP | 2004-065745 A | 3/2004 | |
| JP | 2005-121947 A | 5/2005 | |
| JP | 2005-261514 A | 9/2005 | |
| NL | 1021295 C2 | 2/2004 | |
| SU | 194230 | 5/1967 | |
| SU | 980703 | 12/1982 | |
| WO | WO 84/01707 A1 | 5/1984 | |
| WO | WO 92/13494 A1 | 8/1992 | |
| WO | WO 93/10850 A1 | 6/1993 | |
| WO | WO 93/20760 A1 | 10/1993 | |
| WO | WO 93/20765 A1 | 10/1993 | |
| WO | WO 95/09666 A1 | 4/1995 | |
| WO | WO 96/22056 A1 | 7/1996 | |
| WO | WO 96/27331 A1 | 9/1996 | |
| WO | WO 96/39946 A1 | 12/1996 | |
| WO | WO 97/12557 A1 | 4/1997 | |
| WO | WO 98/01080 A1 | 1/1998 | |
| WO | WO 99/09919 A1 | 3/1999 | |
| WO | WO 99/17661 A1 | 4/1999 | |
| WO | WO 99/30622 A2 | 6/1999 | |
| WO | WO 01/10319 A1 | 2/2001 | |
| WO | WO 01/58360 A2 | 8/2001 | |
| WO | WO 02/11621 A1 | 2/2002 | |
| WO | WO 02/34122 A2 | 5/2002 | |
| WO | WO 02/094082 A2 | 11/2002 | |
| WO | WO 03/045260 A1 | 6/2003 | |
| WO | WO 03/047684 A2 | 6/2003 | |
| WO | WO 03/059412 A2 | 7/2003 | |
| WO | WO 03/078721 A2 | 9/2003 | |
| WO | WO 03/082129 A2 | 10/2003 | |
| WO | WO 2004/006789 A1 | 1/2004 | |
| WO | WO 2004/028613 A2 | 4/2004 | |
| WO | WO 2004/037123 A1 | 5/2004 | |
| WO | WO 2004/052221 A1 | 6/2004 | |
| WO | WO 2004/086984 A1 | 10/2004 | |
| WO | WO 2005/009211 A2 | 2/2005 | |
| WO | WO 2005/018467 A2 | 3/2005 | |
| WO | WO 2005/037088 A2 | 4/2005 | |
| WO | WO 2005/048827 A1 | 6/2005 | |
| WO | WO 2005/065284 A2 | 7/2005 | |
| WO | WO 2005/097019 A2 | 10/2005 | |
| WO | WO 2005/097234 A2 | 10/2005 | |
| WO | WO 2005/112810 A2 | 12/2005 | |
| WO | WO 2005/120363 A1 | 12/2005 | |
| WO | WO 2006/007399 A1 | 1/2006 | |
| WO | WO 2006/041881 A2 | 4/2006 | |
| WO | WO 2006/060405 A2 | 6/2006 | |
| WO | WO 2006/110733 A2 | 10/2006 | |
| WO | WO 2006/113216 A2 | 10/2006 | |
| WO | WO 2007/014063 A2 | 2/2007 | |
| WO | WO 2007/048085 A2 | 4/2007 | |
| WO | WO 2007/063550 A2 | 6/2007 | |
| WO | WO 2007/100067 A1 | 9/2007 | |
| WO | WO 2007/109171 A2 | 9/2007 | |
| WO | WO 2008/005433 A1 | 1/2008 | |
| WO | WO 2008/041225 A2 | 4/2008 | |
| WO | WO 2008/076337 A1 | 6/2008 | |
| WO | WO 2008/076800 A2 | 6/2008 | |
| WO | WO 2008/101075 A2 | 8/2008 | |
| WO | WO 2008/102154 A2 | 8/2008 | |
| WO | WO 2009/021030 A1 | 2/2009 | |
| WO | WO 2009/027065 A1 | 3/2009 | |
| WO | WO 2009/029065 A1 | 3/2009 | |
| WO | WO 2009/032623 A2 | 3/2009 | |
| WO | WO 2010/088481 A1 | 8/2010 | |

OTHER PUBLICATIONS

Ethicon, Inc., "Wound Closure Manual: Chapter 3 (The Surgical Needle)," 15 pages, (publication date unknown).

Guido M. Sclabas, M.D., et al., "Endoluminal Methods for Gastrotomy Closure in Natural Orifice TransEnteric Surgery (NOTES)," Surgical Innovation, vol. 13, No. 1, pp. 23-30, Mar. 2006.

Fritscher-Ravens, et al., "Transgastric Gastropexy and Hiatal Hernia Repair for GERD Under EUS Control: a Porcine Model," Gastrointestinal Endoscopy, vol. 59, No. 1, pp. 89-95, 2004.

Ogando, "Prototype Tools That Go With the Flow," Design News, 2 pages, Jul. 17, 2006.

Edd, et al., "In Vivo Results of a New Focal Tissue Ablation Technique: Irreversible Electroporation," IEEE Trans Biomed Eng, vol. 53, pp. 1409-1415, 2006.

Kennedy, et al., "High-Burst-Strength, Feedback-Controlled Bipolar Vessel Sealing," Surgical Endoscopy, vol. 12, pp. 876-878 (1998).

Collins et al., "Local Gene Therapy of Solid Tumors with GM-CSF and B7-1 Eradicates Both Treated and Distal Tumors," Cancer Gene Therapy, vol. 13, pp. 1061-1071 (2006).
K. Sumiyama et al., "Transesophageal Mediastinoscopy by Submucosal Endoscopy With Mucosal Flap Safety Value Technique," Gastrointest Endosc., Apr. 2007, vol. 65(4), pp. 679-683 (Abstract).
K. Sumiyama et al., "Submucosal Endoscopy with Mucosal Flap Safety Valve," Gastrointest Endosc. Apr. 2007, vol. 65(4) pp. 694-695 (Abstract).
K. Sumiyama et al., "Transgastric Cholecystectomy: Transgastric Accessibility to the Gallbladder Improved with the SEMF Method and a Novel Multibending Therapeutic Endoscope," Gastrointest Endosc., Jun. 2007, vol. 65(7), pp. 1028-1034 (Abstract).
K. Sumiyama et al., "Endoscopic Caps," Tech. Gastrointest. Endosc., vol. 8, pp. 28-32, 2006.
"Z-Offset Technique Used in the Introduction of Trocar During Laparoscopic Surgery," M.S. Hershey NOTES Presentation to EES NOTES Development Team, Sep. 27, 2007.
F.N. Denans, Nouveau Procede Pour La Guerison Des Plaies Des Intestines. Extrait Des Seances De La Societe Royale De Medecine De Marseille, Pendant Le Mois De Dec. 1825, et le Premier Tremestre De 1826, Séance Du 24 Fevrier 1826. Recueil De La Societe Royale De Medecin De Marseille. Marseille: Impr. D'Achard, 1826; 1:127-31. (with English translation).
I. Fraser, "An Historical Perspective on Mechanical Aids in Intestinal Anastamosis," Surg. Gynecol. Obstet. (Oct. 1982), vol. 155, pp. 566-574.
M.E. Ryan et al., "Endoscopic Intervention for Biliary Leaks After Laparoscopic Cholecystectomy: A Multicenter Review," Gastrointest. Endosc., vol. 47(3), 1998, pp. 261-266.
C. Cope, "Creation of Compression Gastroenterostomy by Means of the Oral, Percutaneous, or Surgical Introduction of Magnets: Feasibility Study in Swine," J. Vasc Interv Radiol, (1995), vol. 6(4), pp. 539-545.
J.W. Hazey et al., "Natural Orifice Transgastric Endoscopic Peritoneoscopy in Humans: Initial Clinical Trial," Surg Endosc, (Jan. 2008), vol. 22(1), pp. 16-20.
N. Chopita et al., "Endoscopic Gastroenteric Anastamosis Using Magnets," Endoscopy, (2005), vol. 37(4), pp. 313-317.
C. Cope et al., "Long Term Patency of Experimental Magnetic Compression Gastroenteric Anastomoses Achieved with Covered Stents," Gastrointest Endosc, (2001), vol. 53, pp. 780-784.
H. Okajima et al., "Magnet Compression Anastamosis for Bile Duct Stenosis After Duct to Duct Biliary Reconstruction in Living Donor Liver Transplantation," Liver Transplantation (2005), pp. 473-475.
A. Fritscher-Ravens et al., "Transluminal Endosurgery: Single Lumen Access Anastamotic Device for Flexible Endoscopy," Gastrointestinal Endosc, (2003), vol. 58(4), pp. 585-591.
G.A. Hallenbeck, M.D. et al., "An Instrument for Colorectal Anastamosis Without Sutrues," Dis Col Rectum, (1963), vol. 5, pp. 98-101.
T. Hardy, Jr., M.D. et al., "A Biofragmentable Ring for Sutureless Bowel Anastomosis. An Experimental Study," Dis Col Rectum, (1985), vol. 28, pp. 484-490.
P. O'Neill, M.D. et al., "Nonsuture Intestinal Anastomosis," Am J. Surg, (1962), vol. 104, pp. 761-767.
C.P. Swain, M.D. et al., "Anastomosis at Flexible Endoscopy: An Experimental Study of Compression Button Gastrojejunostomy," Gastrointest Endosc, (1991), vol. 37, pp. 628-632.
J.B. Murphy, M.D., "Cholecysto-Intestinal, Gastro-Intestinal, Entero-Intestinal Anastomosis, and Approximation Without Sutures (original research)," Med Rec, (Dec. 10, 1892), vol. 42(24), pp. 665-676.
USGI® EndoSurgical Operating System—g-Prox® Tissue Grasper/Approximation Device; [online] URL: http://www.usgimedical.com/eos/components-gprox.htm—accessed May 30, 2008 (2 pages).
Printout of web page—http://www.vacumed.com/zcom/product/Product.do?compid=27&prodid=852, #51XX Low-Cost Permanent Tubes 2MM ID, Smooth Interior Walls, VacuMed, Ventura, California, Accessed Jul. 24, 2007.
Endoscopic Retrograde Cholangiopancreatogram (ERCP); [online] URL: http://www.webmd.com/digestive-disorders/endoscopic-retrograde-cholangiopancreatogram-ercp.htm; last updated: Apr. 30, 2007; accessed: Feb. 21, 2008 (6 pages).
ERCP; Jackson Siegelbaum Gastroenterology; [online] URL: http://www.gicare.com/pated/epdgs20.htm; accessed Feb. 21, 2008 (3 pages).
D.G. Fong et al., "Transcolonic Ventral Wall Hernia Mesh Fixation in a Porcine Model," Endoscopy 2007; 39: 865-869.
B. Rubinsky, Ph.D., "Irreversible Electroporation in Medicine," Technology in Cancer Research and Treatment, vol. 6, No. 4, Aug. 2007, pp. 255-259.
D.B. Nelson, MD et al., "Endoscopic Hemostatic Devices," Gastrointestinal Endoscopy, vol. 54, No. 6, 2001, pp. 833-840.
CRE™ Pulmonary Balloon Dilator; [online] URL: http://www.bostonscientific.com/Device.bsci?page=HCP_Overview&navRe1Id=1000.1003&method=D..., accessed Jul. 18, 2008 (4 pages).
J.D. Paulson, M.D., et al., "Development of Flexible Culdoscopy," The Journal of the American Association of Gynecologic Laparoscopists, Nov. 1999, vol. 6, No. 4, pp. 487-490.
H. Seifert, et al., "Retroperitoneal Endoscopic Debridement for Infected Peripancreatic Necrosis," The Lancet, Research Letters, vol. 356, Aug. 19, 2000, pp. 653-655.
K.E. Mönkemüller, M.D., et al., "Transmural Drainage of Pancreatic Fluid Collections Without Electrocautery Using the Seldinger Technique," Gastrointestinal Endoscopy, vol. 48, No. 2, 1998, pp. 195-200, (Received Oct. 3, 1997; Accepted Mar. 31, 1998).
U.S. Appl. No. 12/019,461, filed Jan. 24, 2008.
U.S. Appl. No. 12/045,318, filed Mar. 10, 2008.
U.S. Appl. No. 12/115,916, filed May 6, 2008.
U.S. Appl. No. 12/122,031, filed May 16, 2008.
U.S. Appl. No. 12/129,784, filed May 30, 2008.
U.S. Appl. No. 12/129,880, filed May 30, 2008.
U.S. Appl. No. 12/130,010, filed May 30, 2008.
U.S. Appl. No. 12/130,023, filed May 30, 2008.
U.S. Appl. No. 12/130,224, filed May 30, 2008.
U.S. Appl. No. 12/130,652, filed May 30, 2008.
U.S. Appl. No. 12/133,109, filed Jun. 4, 2008.
U.S. Appl. No. 12/133,953, filed Jun. 5, 2008.
U.S. Appl. No. 12/163,255, filed Jun. 27, 2008.
U.S. Appl. No. 12/169,868, filed Jul. 9, 2008.
U.S. Appl. No. 12/170,862, filed Jul. 10, 2008.
U.S. Appl. No. 12/172,752, filed Jul. 14, 2008.
U.S. Appl. No. 12/172,766, filed Jul. 14, 2008.
U.S. Appl. No. 12/172,782, filed Jul. 14, 2008.
U.S. Appl. No. 12/192,372, filed Aug. 15, 2008.
U.S. Appl. No. 12/203,330, filed Sep. 3, 2008.
U.S. Appl. No. 12/197,749, filed Aug. 25, 2008.
U.S. Appl. No. 12/197,653, filed Aug. 25, 2008.
U.S. Appl. No. 12/202,740, filed Sep. 2, 2008.
U.S. Appl. No. 12/203,458, filed Sep. 3, 2008.
U.S. Appl. No. 12/201,812, filed Aug. 29, 2008.
U.S. Appl. No. 12/207,306, filed Sep. 9, 2008.
U.S. Appl. No. 12/243,334, filed Oct. 1, 2008.
U.S. Appl. No. 12/234,425, filed Sep. 19, 2008.
U.S. Appl. No. 12/060,601, filed Apr. 1, 2008.
U.S. Appl. No. 12/277,975, filed Nov. 25, 2008.
U.S. Appl. No. 12/277,957, filed Nov. 25, 2008.
U.S. Appl. No. 12/332,938, filed Dec. 11, 2008.
U.S. Appl. No. 12/337,340, filed Dec. 17, 2008.
U.S. Appl. No. 12/352,451, filed Jan. 12, 2009.
U.S. Appl. No. 12/359,824, filed Jan. 26, 2009.
U.S. Appl. No. 12/352,375, filed Jan. 12, 2009.
U.S. Appl. No. 12/359,053, filed Jan. 23, 2009.
U.S. Appl. No. 12/362,826, filed Jan. 30, 2009.
U.S. Appl. No. 12/363,137, filed Jan. 30, 2009.
U.S. Appl. No. 12/364,256, filed Feb. 2, 2009.
U.S. Appl. No. 12/413,479, filed Mar. 27, 2009.
U.S. Appl. No. 12/468,462, filed May 19, 2009.
International Search Report for PCT/US2010/022711, Jun. 16, 2010 (7 pages).
D. Wilhelm et al., "An Innovative, Safe and Sterile Sigmoid Access (ISSA) for NOTES," Endoscopy 2007, vol. 39, pp. 401-406.

Nakazawa et al., "Radiofrequency Ablation of Hepatocellular Carcinoma: Correlation Between Local Tumor Progression After Ablation and Ablative Margin," AJR, 188, pp. 480-488 (Feb. 2007).

Miklavčič et al., "A validated model of in vivo electric field distribution in tissues for electrochemotherapy and for DNA electrotransfer for gene therapy," Biochimica et Biophysica Acta, 1523, pp. 73-83 (2000).

Evans, "Ablative and cathether-delivered therapies for colorectal liver metastases (CRLM)," EJSO, 33, pp. S64-S75 (2007).

Wong et al., "Combined Percutaneous Radiofrequency Ablation and Ethanol Injection for Hepatocellular Carcinoma in High-Risk Locations," AJR, 190, pp. W187-W195 (2008).

Heller et al., "Electrically mediated plasmid DNA delivery to hepatocellular carcinomas in vivo," Gene Therapy, 7, pp. 826-829 (2000).

Widera et al., "Increased DNA Vaccine Delivery and Immunogenicity by Electroporation in Vivo," The Journal of Immunology, 164, pp. 4635-4640 (2000).

Weaver et al., "Theory of electroporation: A review," Bioelectrochemistry and Bioenergetics, 41, pp. 135-160 (1996).

Mulier et al., "Radiofrequency Ablation Versus Resection for Resectable Colorectal Liver Metastases: Time for a Randomized Trial?" Annals of Surgical Oncology, 15(1), pp. 144-157 (2008).

Link et al., "Regional Chemotherapy of Nonresectable Colorectal Liver Metastases with Mitoxanthrone, 5-Fluorouracil, Folinic Acid, and Mitomycin C May Prolong Survival," Cancer, 92, pp. 2746-2753 (2001).

Guyton et al., "Membrane Potentials and Action Potentials," W.B. Sanders, ed. Textbook of Medical Physiology, p. 56 (2000).

Guyton et al., "Contraction of Skeletal Muscle," Textbook of Medical Physiology, pp. 82-84 (2000).

"Ethicon Endo-Surgery Novel Investigational Notes and SSL Devices Featured in 15 Presentations at Sages," Apr. 22, 2009 Press Release; URL http://www.jnj.com/connect/news/all/20090422_152000; accessed Aug. 28, 2009 (3 pages).

"Ethicon Endo-Surgery Studies Presented At DDW Demonstrate Potential of Pure NOTES Surgery With Company's Toolbox," Jun. 3, 2009 Press Release; URL http://www.jnj.com/connect/news/product/20090603_120000; accessed Aug. 28, 2009 (3 pages).

Castellvi et al., "Hybrid Transvaginal NOTES Sleeve Gastrectomy in a Porcine Model Using a Magnetically Anchored Camera and Novel Instrumentation," Abstract submitted along with Poster at SAGES Annual Meeting in Phoenix, AZ, Apr. 22, 2009 (1 page).

OCTO Port Modular Laparoscopy System for Single Incision Access, Jan. 4, 2010; URL http://www.medgadget.com/archives/2010/01/octo_port_modular_laparo...; accessed Jan. 5, 2010 (4 pages).

Hakko Retractors, obtained Aug. 25, 2009 (5 pages).

Zadno et al., "Linear Superelasticity in Cold-Worked NI-TI," Engineering Aspects of Shape Memory Alloys, pp. 414-419.

U.S. Appl. No. 12/607,252, filed Oct. 28, 2009.
U.S. Appl. No. 12/580,400, filed Oct. 16, 2009.
U.S. Appl. No. 12/607,388, filed Oct. 28, 2009.
U.S. Appl. No. 12/612,911, filed Nov. 5, 2009.
U.S. Appl. No. 12/614,143, filed Nov. 6, 2009.
U.S. Appl. No. 12/617,998, filed Nov. 13, 2009.
U.S. Appl. No. 12/640,440, filed Dec. 17, 2009.
U.S. Appl. No. 12/640,469, filed Dec. 17, 2009.
U.S. Appl. No. 12/640,476, filed Dec. 17, 2009.
U.S. Appl. No. 12/640,492, filed Dec. 17, 2009.
U.S. Appl. No. 12/641,823, filed Dec. 18, 2009.
U.S. Appl. No. 12/641,853, filed Dec. 18, 2009.
U.S. Appl. No. 12/641,837, filed Dec. 18, 2009.
U.S. Appl. No. 12/651,181, filed Dec. 31, 2009.
U.S. Appl. No. 12/696,598, filed Jan. 29, 2010.
U.S. Appl. No. 12/696,626, filed Jan. 29, 2010.
U.S. Appl. No. 12/752,701, filed Apr. 1, 2010.

Zadno et al., "Linear Superelasticity in Cold-Worked NI—TI," Engineering Aspects of Shape Memory Alloys, pp. 414-419 (1990).

U.S. Appl. No. 13/013,131, filed Jan. 25, 2011.
U.S. Appl. No. 13/013,147, filed Jan. 25, 2011.
U.S. Appl. No. 12/900,132, filed Oct. 7, 2010.
U.S. Appl. No. 12/939,441, filed Nov. 4, 2010.
U.S. Appl. No. 12/902,531, filed Oct. 12, 2010.
U.S. Appl. No. 12/902,550, filed Oct. 12, 2010.

* cited by examiner

SURGICAL SCISSORS

BACKGROUND

Various embodiments are directed to surgical scissors devices and methods of manufacturing and using the same.

Minimally invasive procedures are desirable because such procedures can reduce pain and provide relatively quick recovery times as compared to conventional open medical procedures. Many minimally invasive procedures are performed with an endoscope (including without limitation laparoscopes). Such procedures permit a physician to position, manipulate, and view medical instruments and accessories inside the patient through a small access opening in the patient's body. Laparoscopy is a term used to describe such an "endosurgical" approach using an endoscope (often a rigid laparoscope). In this type of procedure, accessory devices are often inserted into a patient through trocars placed through the body wall. Still less invasive treatments include those that are performed through insertion of an endoscope through a natural body orifice to a treatment region. Examples of this approach include, but are not limited to, cystoscopy, hysteroscopy, esophagogastroduodenoscopy, and colonoscopy.

Many of these procedures employ a flexible endoscope during the procedure. Flexible endoscopes often have a flexible, steerable articulating section near the distal end that can be controlled by the clinician by utilizing controls at the proximal end. Some flexible endoscopes are relatively small (1 mm to 3 mm in diameter), and may have no integral accessory channel (also called biopsy channels or working channels). Other flexible endoscopes, including gastroscopes and colonoscopes, have integral working channels having a diameter of about 2.0 to 3.7 mm for the purpose of introducing and removing medical devices and other accessory devices to perform diagnosis or therapy within the patient. Certain specialized endoscopes are available, such as large working channel endoscopes having a working channel of 5 mm in diameter, which can be used to pass relatively large accessories, or to provide capability to suction large blood clots. Other specialized endoscopes include those having two or more working channels.

FIGURES

The novel features of the various embodiments are set forth with particularity in the appended claims. The various embodiments, however, both as to organization and methods of operation, together with advantages thereof, may best be understood by reference to the following description, taken in conjunction with the accompanying drawings as follows.

DESCRIPTION

Various embodiments are directed to surgical scissors devices. The surgical scissors devices may, for example, be deployed through the working channel of an endoscope. The surgical scissors devices described herein may have various features for enhancing performance. For example, various embodiments may have blade members that are held in compression relative to one another by a fastener. This may tend to hold the blade members together during use and prevent or minimize tissue slipping between the scissor blades. Also, in various embodiments, the blade members of the scissors device may be cam actuated. This may allow increased mechanical advantage, allowing the clinician to more easily open and close the blade members.

Various other embodiments described herein are directed to methods and devices for constructing surgical scissors. For example, according to some embodiments, a compressive force may be applied to the first and second blade members, tending to push them together. While the compressive force is applied, a fastener may be installed to hold the blade members together. Then the compressive force may be released. The fastener may serve to maintain the blade members in compression against one another. The compressive force may be applied by any suitable mechanism including, for example, a clamp having a first clamp member, a second clamp member and a clamp mechanism, as described herein. One or more of the clamp members may define a cavity shaped to receive one or both the blade members. This may secure the blade members while the compressive force is applied.

Figure 1:
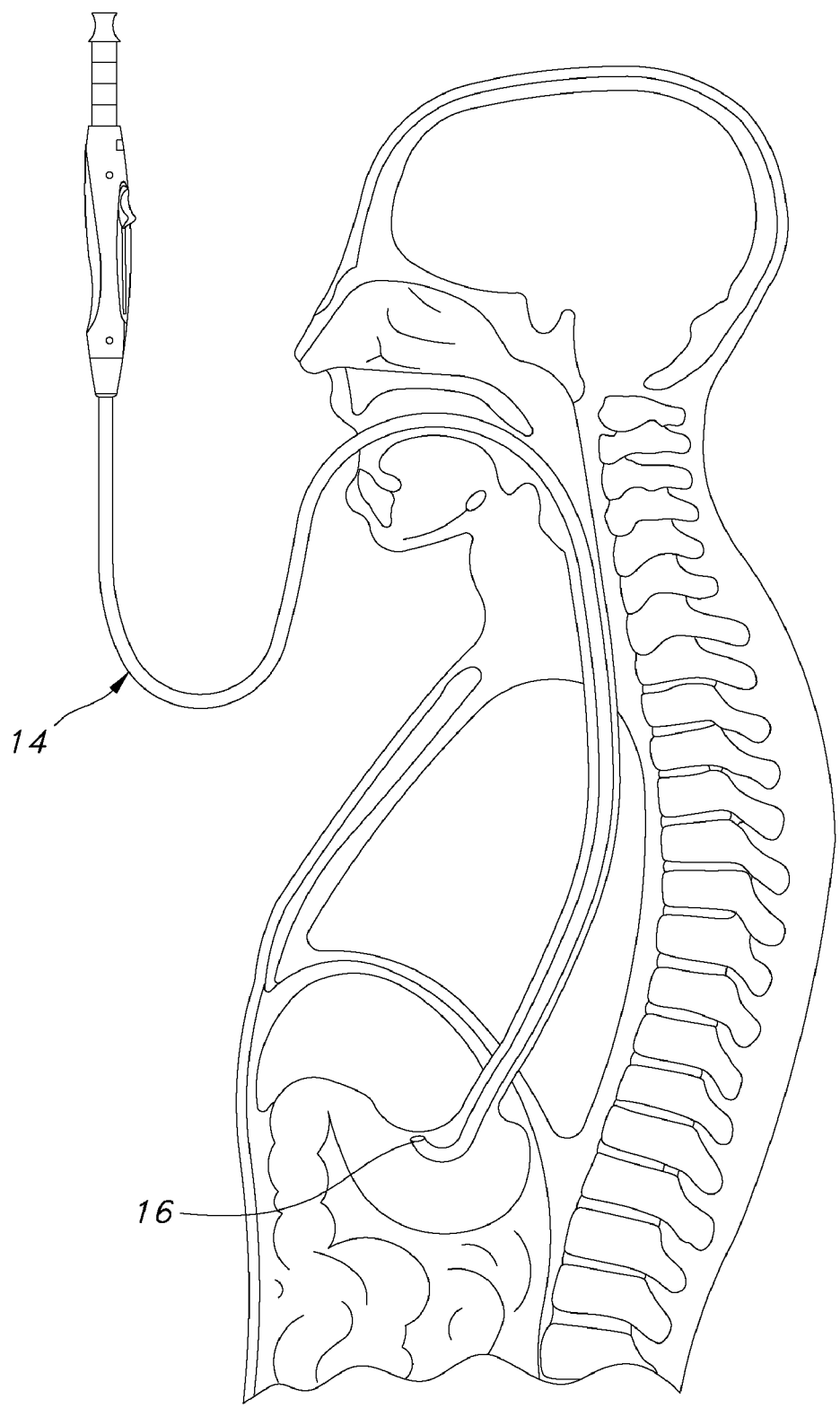
FIG. 1 illustrates one embodiment of an endoscope inserted into the upper gastrointestinal tract of a patient.

Various embodiments of the surgical scissors devices described herein may be used in endoscopic surgical environments. FIG. 1 illustrates one embodiment of an endoscope 14 (illustrated here as a gastroscope) inserted into the upper gastrointestinal tract of a patient. The endoscope 14 has a distal end 16 that may include various optical channels, illumination channels, and working channels. According to various embodiments, the endoscope 14 may be a flexible endoscope, and may be introduced via natural orifices.

In one embodiment, Natural Orifice Translumenal Endoscopic Surgery (NOTES)™ techniques may be employed to introduce the endoscope 14 and various instruments (e.g., the surgical scissors devices described herein) into the patient and carry out the various procedures described herein. A NOTES™ technique is a minimally invasive therapeutic procedure that may be employed to treat diseased tissue or perform other therapeutic operations through a natural opening of the patient without making incisions in the abdomen. A natural opening may be the mouth, anus, and/or vagina. Medical implantable instruments may be introduced into the patient to the target area via the natural opening. In a NOTES™ technique, a clinician inserts a flexible endoscope into one or more natural openings of the patient to view the target area, for example, using a camera. During endoscopic surgery, the clinician inserts surgical devices through one or more lumens or working channels of the endoscope 14 to perform various key surgical activities (KSA). These KSAs include forming an anastomosis between organs, performing dissections, repairing ulcers and other wounds. Although the devices and methods described herein may be used with NOTES™ techniques, it will be appreciated that they may also be used with other surgical techniques including, for example, other endoscopic techniques and laparoscopic techniques.

Figure 2:
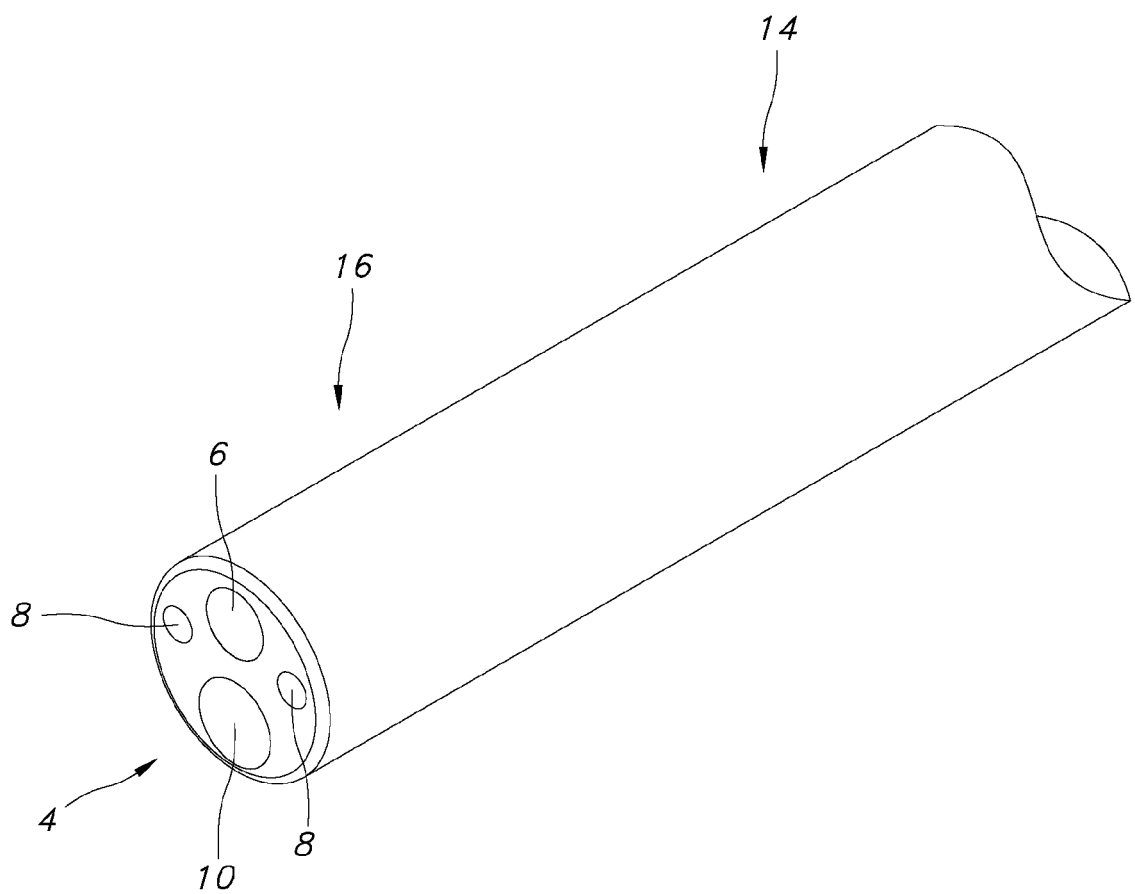
FIG. 2 illustrates one embodiment of a distal portion of the endoscope of FIG. 1, which may be used with the scissors devices described herein.

FIG. 2 illustrates one embodiment of a distal portion 16 of the endoscope 14, which may be used with the scissors devices described herein. The example endoscope 14 shown comprises a distal face 4, which defines the distal ends of illumination channels 8, an optical channel 6 and a working channel 10. The illumination channels 8 may comprise one or more optical fibers or other suitable waveguides for directing light from a proximally positioned light source (not shown) to the surgical site. The optical channel 6 may comprise one or more optical fibers or other suitable waveguides for receiving and transmitting an image of the surgical site proximally to a position where the image may be viewed by the clinician operating the endoscope 14. As described above, the working channel 10 may allow the clinician to introduce one or more surgical tools to the surgical site. Examples of such surgical tools include scissors, cautery knives, suturing devices and scissors devices. It will be appreciated that the endoscope 14 is but one example of an endoscope that may be used in accordance with various embodiments. Endoscopes having alternate configurations of optical channels 6, illumination channels 8 and/or working channels 10 may also be used.

Figure 3:
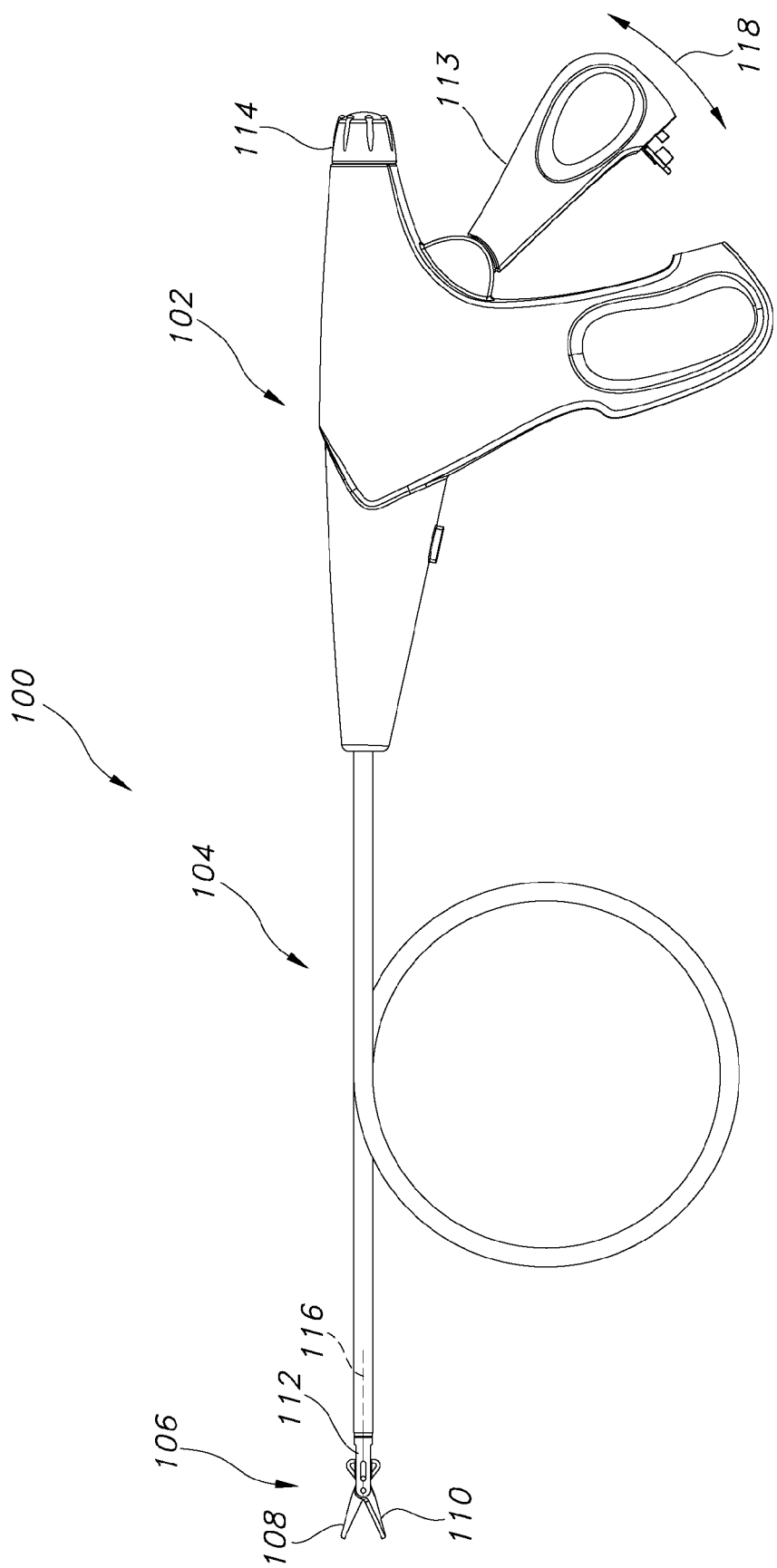
FIG. 3 illustrates one embodiment of a scissors device, which may be used, with the endoscope of FIG. 1.
Figure 4:
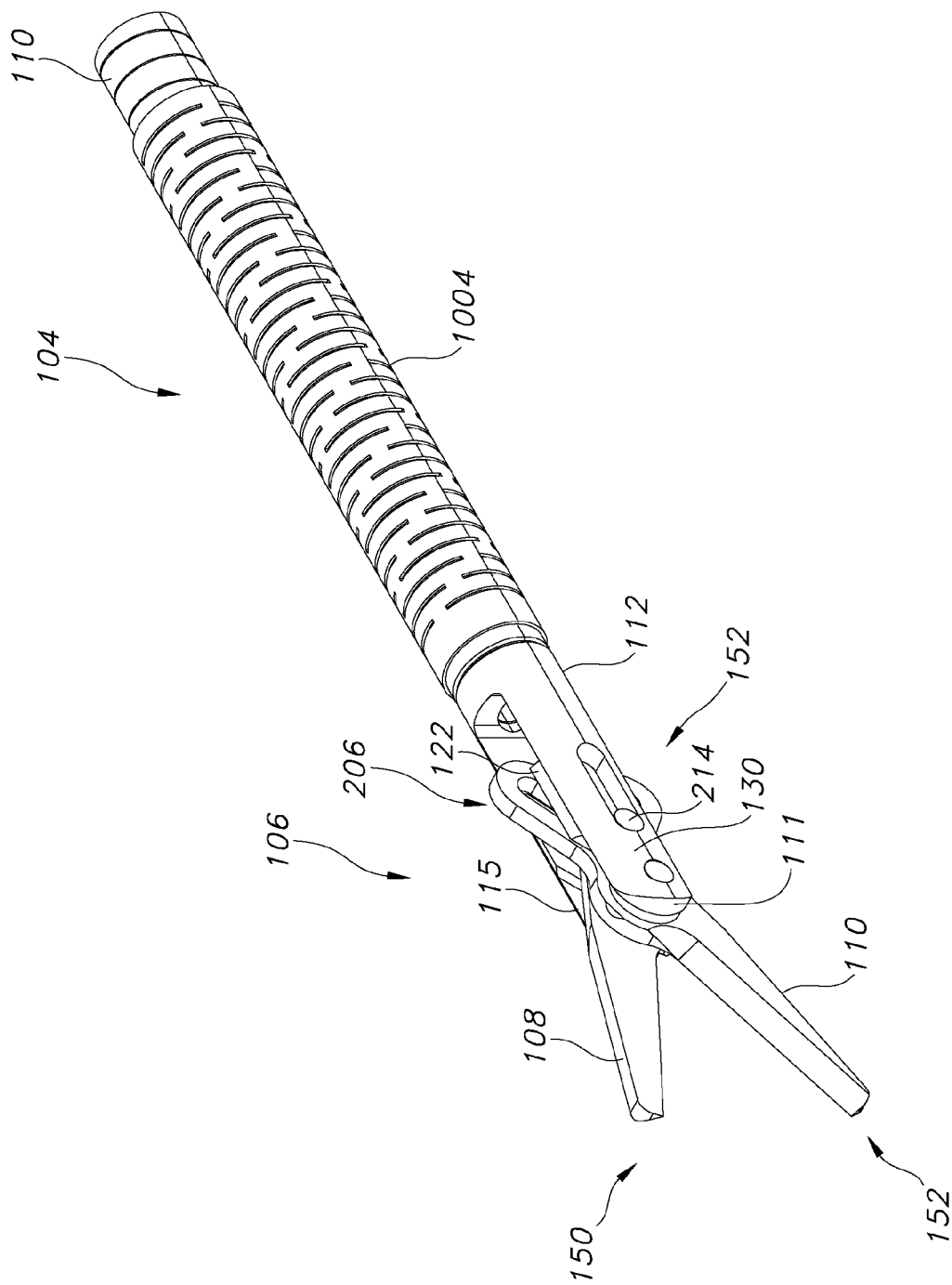
FIG. 4 illustrates one embodiment of the end effector of the scissors device of FIG. 3.

FIG. 3 illustrates one embodiment of a scissors device 100, which may be used, for example, with an endoscope such as the endoscope 14. The scissors device 100 may comprise a handle assembly 102, a flexible shaft 104 and an end effector 106. The end effector 106 may comprise a first blade member 108 and a second blade member 110. The first blade member 108 and second blade member 110 may be connected to a clevis 112, which, in turn, may be coupled to the flexible shaft 104. FIG. 4 illustrates one embodiment of the end effector 106 of the scissors device 100. The blade members 108, 110 may have respective blade ends 150, 152 and cam ends 206, 208. The blade members may be configures such that the blade ends 150, 152 overlap one another in the open position. In some example embodiments, the overlap may be between about 0.127 mm (0.005 inches) and 0.152 mm (0.006 inches). The blade members 108, 110 may pivot about a pivot point 130 that may comprise a pin or other connector to fasten the blade members 108, 110 to one another, or to fasten the blade members 108, 110 between arms 111, 115 of the clevis 112, which may hold them together. The respective arms 111, 115 of the clevis may each define a pin hole that aligns with the pivot point 130 and may receive the fastener. A shuttle 122 may comprise one or more pin features 214 received into one or more cam slots 210, 212 of the respective blade members 108, 110, for example, as described herein below. The shuttle 122 may be coupled to a translating member 116, which may extend proximally through the flexible shaft 104 to the handle 102.

Referring back to FIG. 3, the translating member 116 may extend within the flexible shaft 104 from the end effector 106 to the handle 102. The translating member 116 may be made from any suitable material. For example, the translating member 116 may be, a metal wire (e.g., a multi-layered steel cable, such as a tri-layered steel cable), a plastic or metal shaft. According to various embodiments, the translating member may comprise a spiral cut or otherwise slotted hypotube (e.g., a cylindrical object with slots cut therein to provide or enhance flexibility). For example, in FIG. 4, the translating member 116 is illustrated as comprising a cut hypotube. At the handle 102, the flexible shaft 104 may be directly or indirectly coupled to an actuator 113. In use, a clinician may cause the actuator 113 to pivot along arrow 118 from a first position to a second position. When the actuator 113 moves from the first position to the second position, it may translate the translating member 116 distally or proximally. Distal or proximal motion of the translating member 116 may, in turn, cause the end effector 106 to transition from an open position to a closed position. Repeatedly transitioning the end effector 106 from the open position to the closed position may affect cutting of tissue or other materials.

Figure 5:
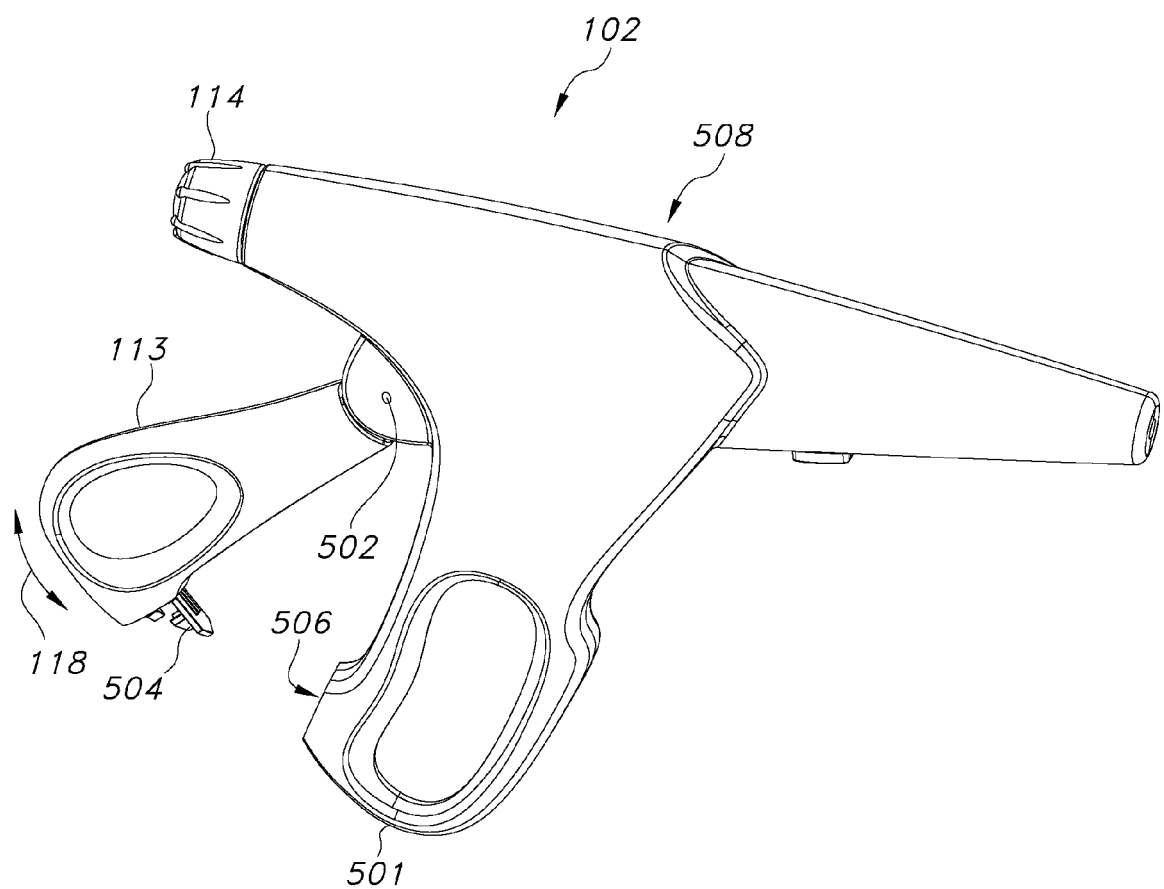
FIG. 5 illustrates one embodiment of the handle of the scissors device of FIG. 3.

FIG. 5 illustrates one embodiment of the handle 102 of the scissors device 100. The actuator 113 may pivot about pivot point 502 along arrow 118 as shown. The pivot point 502 may comprise a pin or other connector fastening the actuator to the handle body 508. The handle body 508 may define a grip 501 opposite the actuator 113 as shown. In one example, use, the clinician may place one or more fingers through the grip 501, allowing the clinician to manipulate the actuator 113 with a thumb. According to various embodiments, the actuator 113 may comprise a lock element 504 configured to be securely received into a lock cavity 506. The lock element 504 and cavity 506 may allow the clinician to secure the actuator 113, and thus the end effector 106, into a given position.

Figure 6:
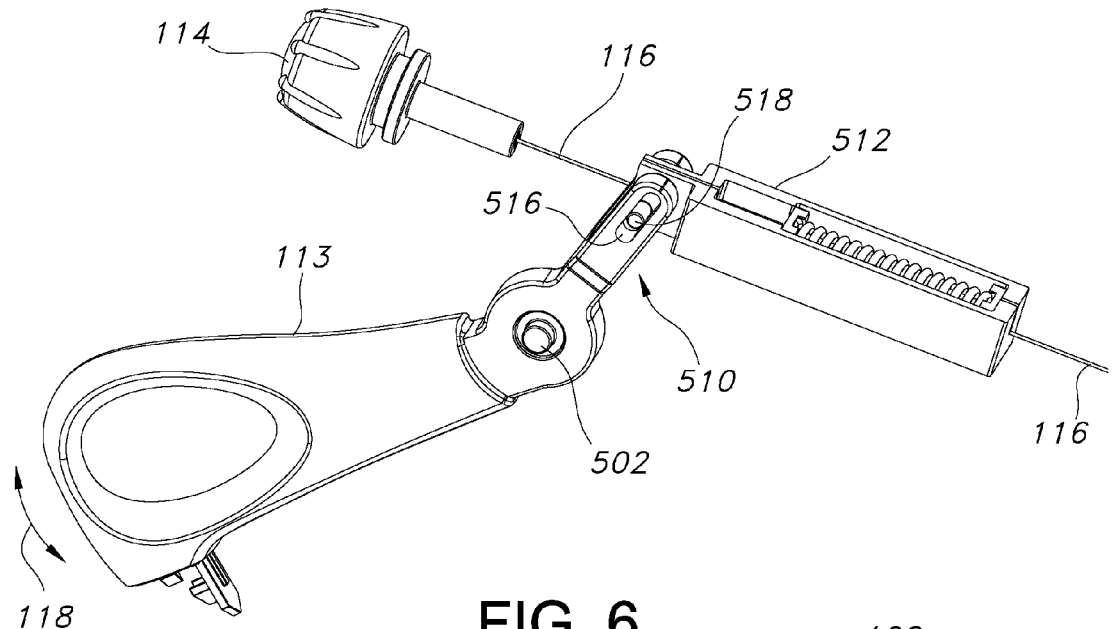
FIG. 6 illustrates one embodiment of the handle of FIG. 5 with the handle body not shown.
Figure 7:
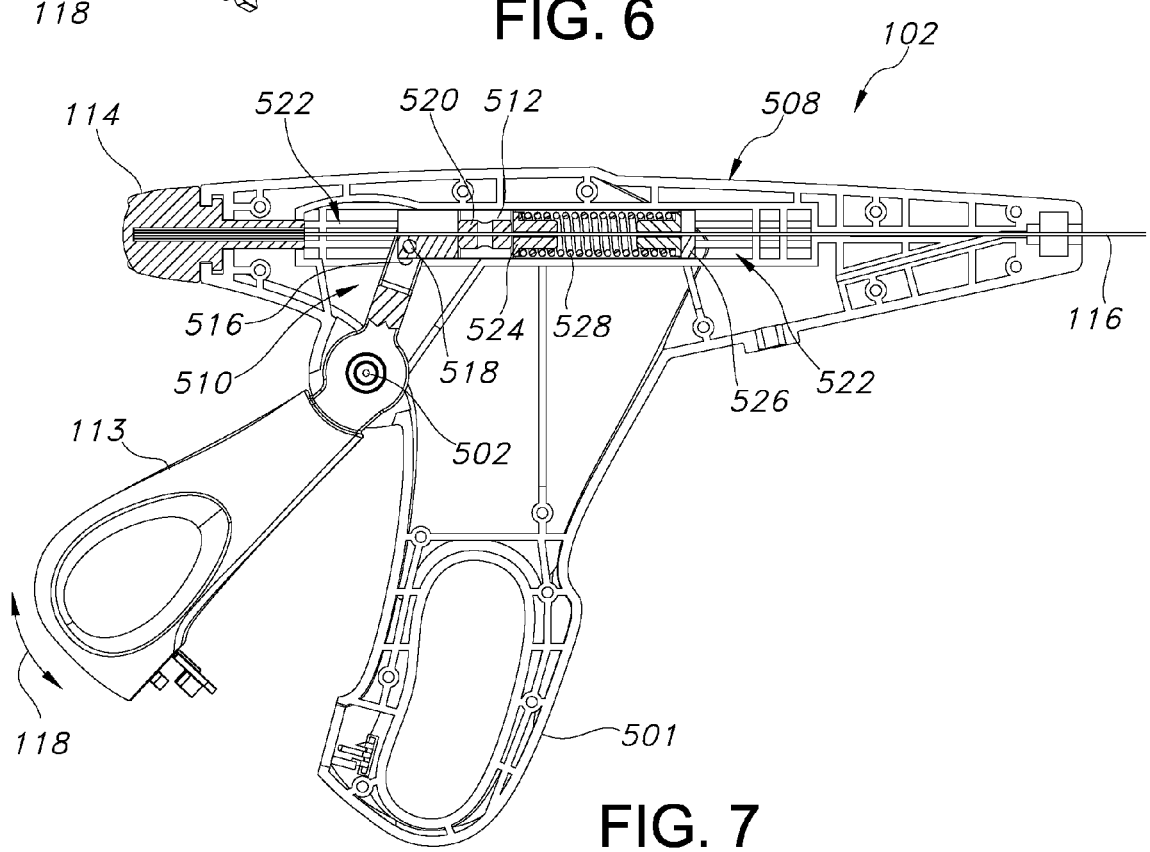
FIG. 7 illustrates a cross section of one embodiment of the handle of FIG. 5.
Figure 8:
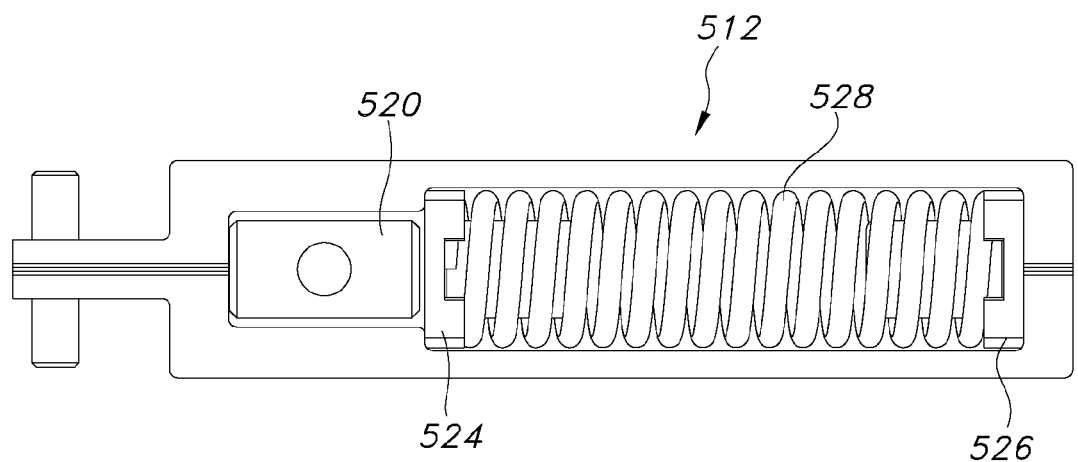
FIG. 8 illustrates one embodiment of a slider mechanism from the handle of FIG. 5.

FIG. 6 illustrates one embodiment of the handle 102 with the handle body 508 not shown. The actuator 113 is shown with a pair of arms 510 defining slots 516. The arms 510 receive a pin 518 to slidably couple the actuator to a slider mechanism 512. FIG. 7 illustrates a cross section of one embodiment of the handle 102. FIG. 8 illustrates one embodiment of the slider mechanism 512. The translating member 116 is received at the distal portion of the handle body 508 and extends proximally to the slider mechanism 512. Within the slider mechanism 512, the translating member 116 may be received by a pair of spring holders 524, 526 and a collar 520. From the collar 528, the translating member 116 may extend proximally to the rotation knob 114. The translating member 116 may be securely fastened to the collar 520 such that the translating member 116 cannot translate distally and proximally with respect to the collar 520.

In use, the clinician may move the actuator 113 towards the grip 501 to force the translating member 116 proximally. The resulting rotation of the actuator 113 about the pivot point 502 may pull the slider mechanism 512 proximally within the cavity 522 defined by the handle body 508. This may also pull the collar 520 and translating member 116 proximally. Spring 528 may resist motion of the slider mechanism 512 and thus the translating member 116. To move the translating member 116 distally, the clinician may pivot the actuator 113 away from the grip 501 about the pivot point 502. This may force the slider mechanism 512 and thus the translating member 116 distally.

Figure 9:
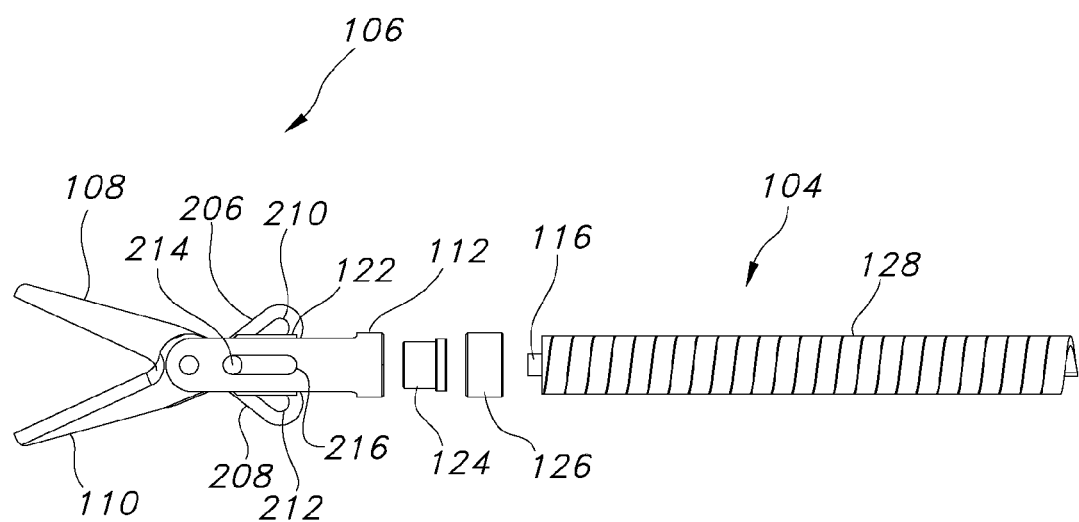
FIG. 9 is an exploded view of the end effector and flexible shaft of one embodiment of the scissors device of FIG. 3 having cam-actuated blades.

FIG. 9 illustrates an exploded view of the end effector 106 and flexible shaft 104 of one embodiment of the scissors device 100 having cam-actuated blade members. As shown, the blade members 108, 110 comprise the proximal cam ends 206, 208. Each of the cam ends 206, 208 defines a respective cam slot 210, 212. A shuttle 122 may comprise one or more pin features 214 that ride in the cam slots 210, 212. For example, the shuttle 122 may comprise a single pin feature 214 extending through both sides or separate pin features 214 on each side. According to various embodiments, the pin features 214 may also protrude from a slot 216 defined by the clevis 112.

Figure 9A:
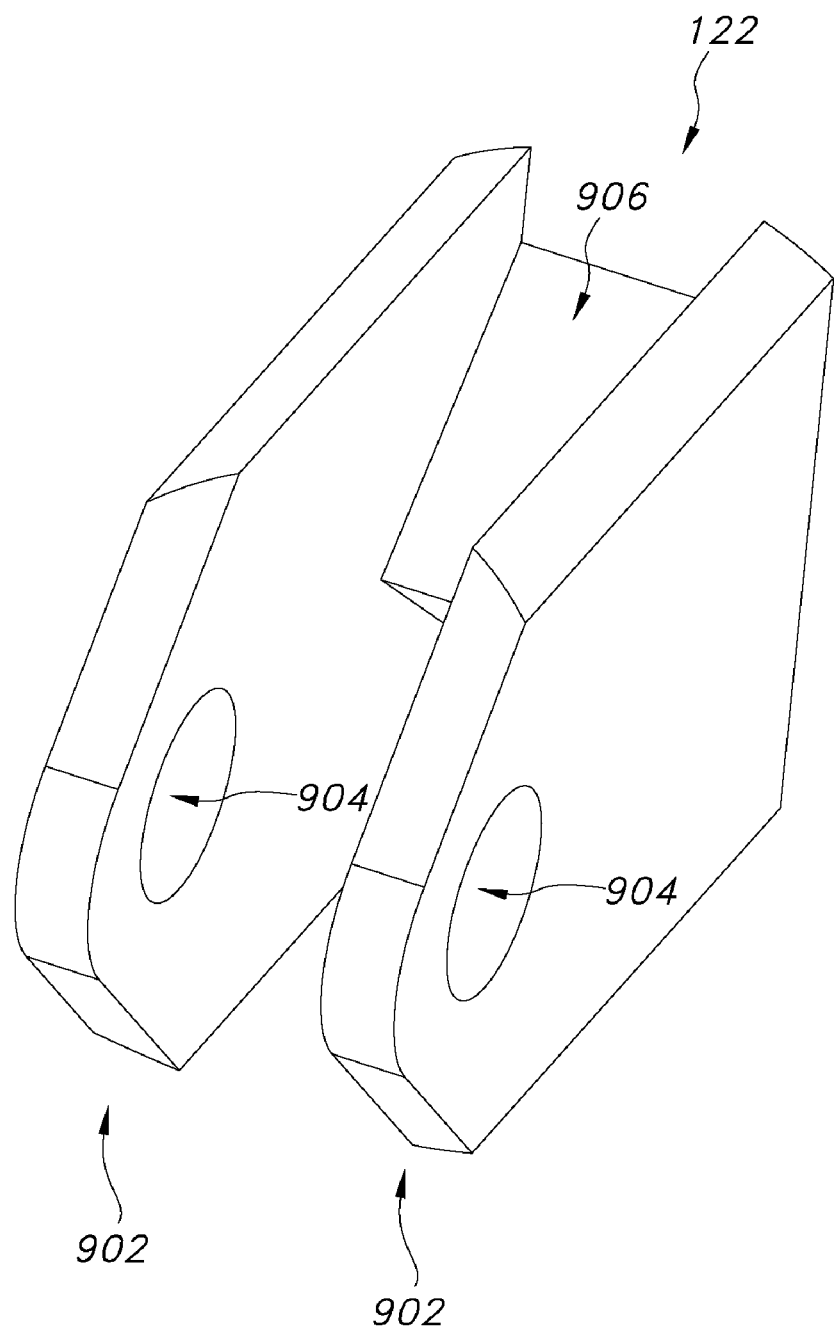
FIG. 9A illustrates one embodiment of a shuttle for use with the end effector of FIG. 9.

FIG. 9A illustrates one embodiment of the shuttle 122. In use, the shuttle 122 may be coupled to the translating member 116. As shown, the shuttle 122 may have two arm members 902 defining holes 904 for receiving the pin feature or features 214. The cam ends 206, 208 of the blade members 108, 110 may be received between the arm members 902. A wedge feature 906 may be positioned at a proximal portion of the shuttle 122 and may serve to wedge the cam ends 206, 208 of the blade members 108, 110 apart from one another when the shuttle 122 is it its distal position. Referring back to FIG. 9, distal motion of the translating member 116 may cause corresponding distal motion of the shuttle 122, which may, in turn, force the pin features 214 to slide within the cam slots 210, 212, forcing the blade members 108, 110 into an open position. In some embodiment, the wedge feature 906 of the shuttle may provide an additional force tending to open the blade members 108, 110 by forcing the cam ends 206, 208 away from one another.

According to various embodiments, the end effector 106 may be rotatably coupled to the flexible shaft 104. For example, an outer coupler 126 may be fastened to the flexible shaft 104. An inner coupler 124 may be fastened within the outer coupler 126 such that the inner coupler 124 can rotate relative to the outer coupler 126 and the flexible shaft 104. The inner coupler 124 may also be coupled to the clevis 112 (and hence the end effector 106). Accordingly, the end effector 106 may be rotatable, with the inner coupler 124, about the outer coupler 126 and the flexible shaft 104. As described above, the translating member 116 may be coupled to the end effector 106, for example, via the shuttle 122. The clinician may bring about rotation of the end effector 106 by rotating the translating member 116. For example, referring to FIG. 5-7, the handle 102 may comprise a knob 114 or other control device allowing the clinician to rotate the translating member 116.

The flexible shaft 104 may be made from any suitable material and/or device. In various embodiments the flexible shaft 104 may be made from a material or device that is flexible and also able to withstand tension and compression forces to avoid significant losses in the opening and closing forces provided by the clinician via the actuator 113. For example, when the actuator 118 causes the translating member 116 to move distally, the flexible shaft 104 may be placed in compression. When the actuator 118 causes the translating member 116 to move proximally, the flexible shaft 104 may be placed in tension. Excessive compression or stretching of the flexible shaft 104 may attenuate the force ultimately provided to open or close the end effector 106.

Figure 10:
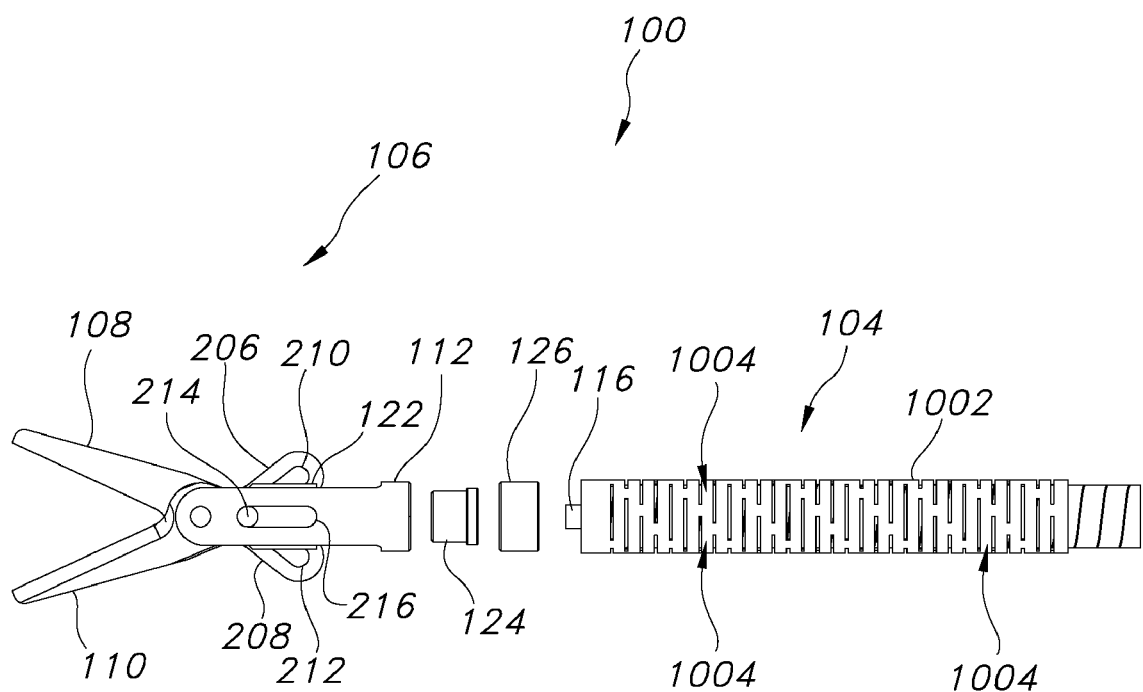
FIG. 10 illustrates one embodiment of the scissors device of FIG. 3 with a flexible shaft comprising a cut hypotube.

In various embodiments, the flexible shaft may comprise a coil pipe 128, as illustrated in FIG. 9. The coil pipe 128 may be made from wire or a narrow ribbon of material formed into a cylindrical coil. The coiled nature of the coil pipe 128 may cause it to perform well in compression. In tension, however, the coil pipe 128 may tend to expand, thus attenuating the force applied to the end effector 106. The attenuation may be minimized by selecting a coil pipe 128 with a high pre-load. This may make the coil pipe 128 relatively stiff and more difficult to bend, but may also improve its performance in tension. FIG. 10 illustrates another embodiment of the scissors device 100 with a flexible shaft 104 comprising a cut hypotube 1002 in place of the coil pipe 128. The cut hypotube 1002 may be a cylindrical piece of material (e.g., surgical steel or other metal) with a plurality of cuts or cut-out features 1004. The cuts may allow the hypotube 1002 to bend. Because the hypotube 1002 may bend on the cuts, the spatial frequency of the cuts in any given portion of the hypotube 1002 may determine the flexibility of that portion. A higher spatial frequency of cuts may correspond to a higher flexibility. Because the hypotube 1002 is not configured to stretch under ordinary operating conditions, it may provide increased tensile performance compared to the coil pipe 128.

Figure 11:
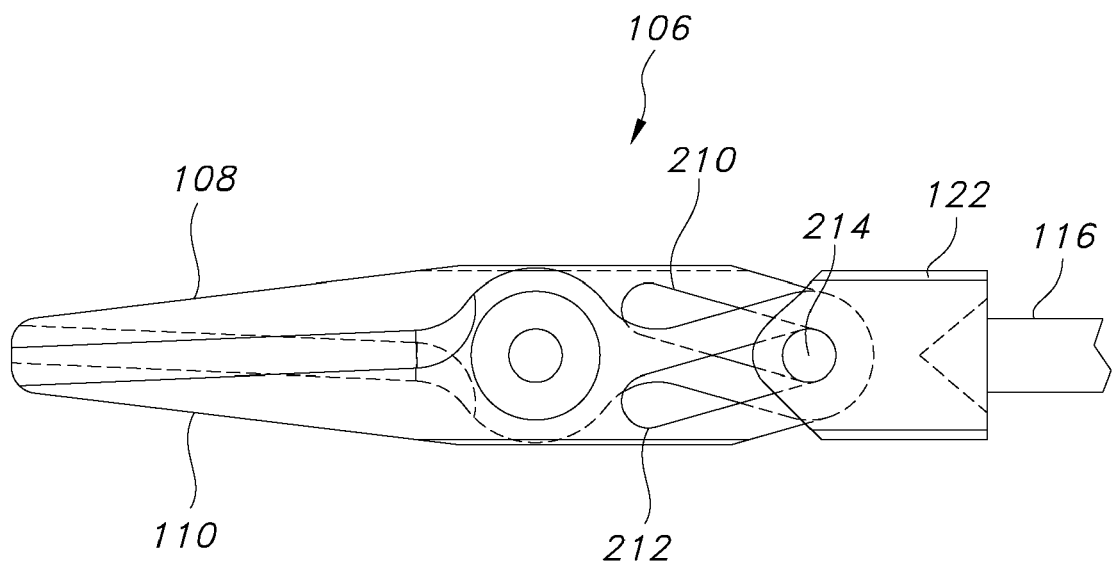
FIGS. 11-14 illustrate one embodiment of the end effector of FIG. 4 transitioning from a closed position shown in FIG. 11 to an open position shown in FIG. 14.
Figure 12:
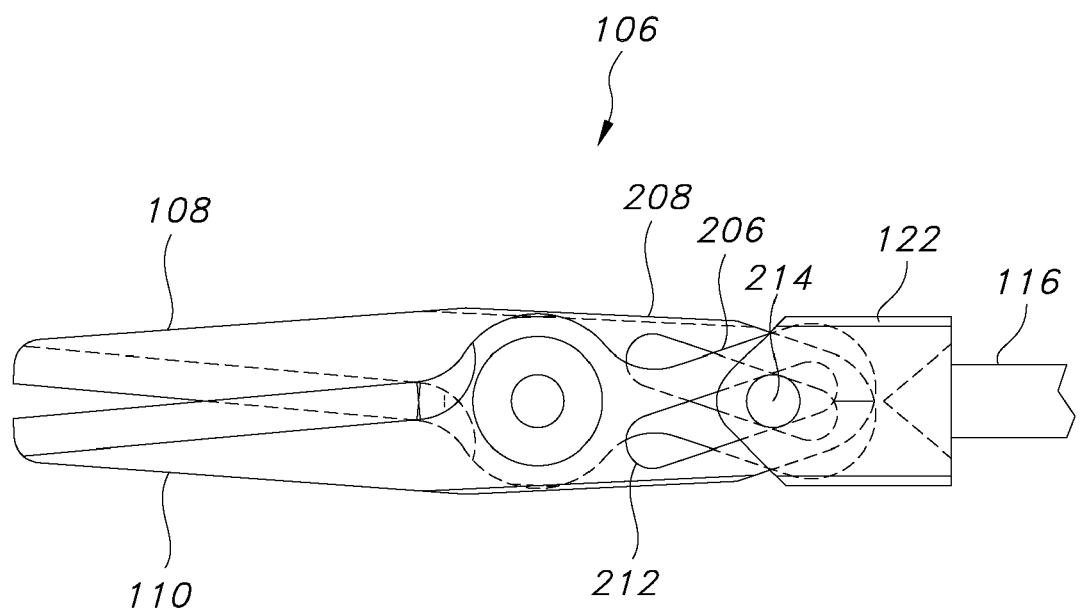
Figure 13:
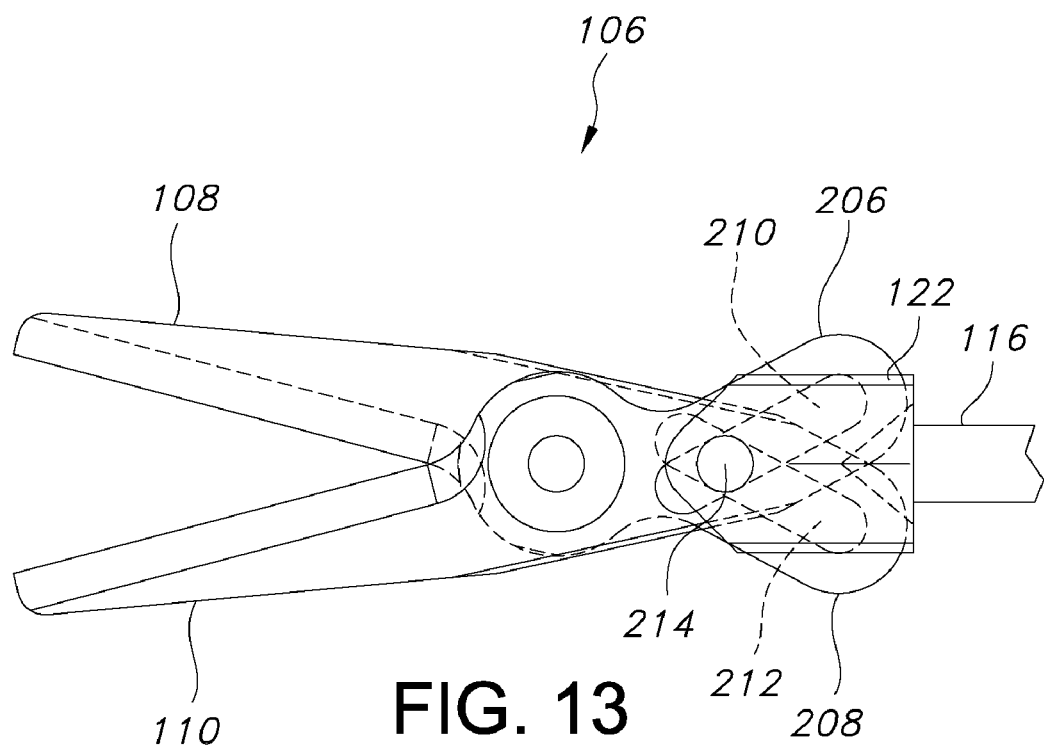
Figure 14:
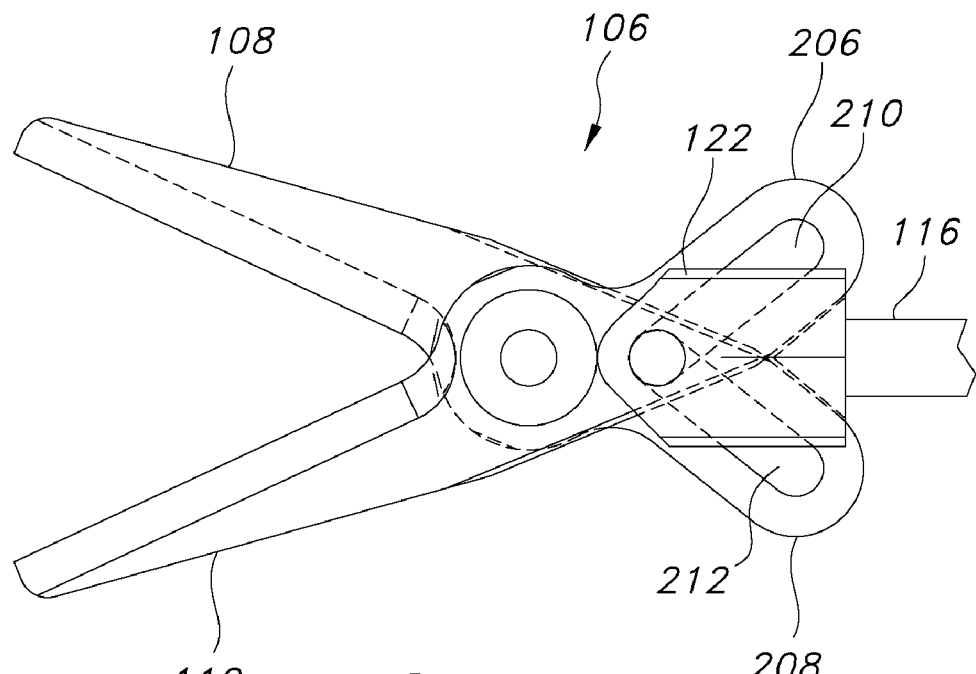

FIGS. 11-14 illustrate one embodiment of the end effector 106 transitioning from a closed position shown in FIG. 11 to an open position shown in FIG. 14. Referring to FIG. 11, the end effector 106 is shown in the closed position. The blade members 108, 110 are illustrated in a closed, overlapping position. The shuttle 122 is shown coupled to the translating member 116 and in a proximal position. For example, a clinician operating the actuator 113 may have caused the translating member 116 to translate through the flexible shaft 104 in a proximal direction. This may, in turn, have caused the shuttle 122 to assume the proximal position shown. When the shuttle 122 is in the proximal position the pins 214 may be positioned within the slots 210, 212 such that the blade members 108, 110 are in the closed position.

FIGS. 12 and 13 illustrate one embodiment of the end effector 106 transitioning from the closed position to the open position. As the translating member 116 and shuttle 122 are pushed distally, the pins 214 may also move distally within the cam slots 210, 212. Due to the curvature of the cam slots 210, 212, this may force the blade members 108, 110 into the open position. In FIG. 14, the end effector 106 is shown with the shuttle 122 in its fully distal position and the blade members 108, 110 in their fully open position. It will be appreciated that the profile (e.g., shape) of the cam slots 210, 212, may bring about a mechanical advantage, lessening the force necessary to open or close the end effectors 106. For example, configuring the cam slots 210, 212 with a shallow profile may reduce the mechanical advantage between the actuator 113 and the end effector 106. This may, in turn, minimize the movement of the actuator 113 that is necessary to open the end effector 106, but maximize the required force. Similarly, configuring the cam slots 210, 212 with a more curved profile may increase the mechanical advantage between the actuator 113 and the end effector 106. This may decrease the force that the clinician must apply to the actuator 113, but increase the necessary movement.

Figure 15:
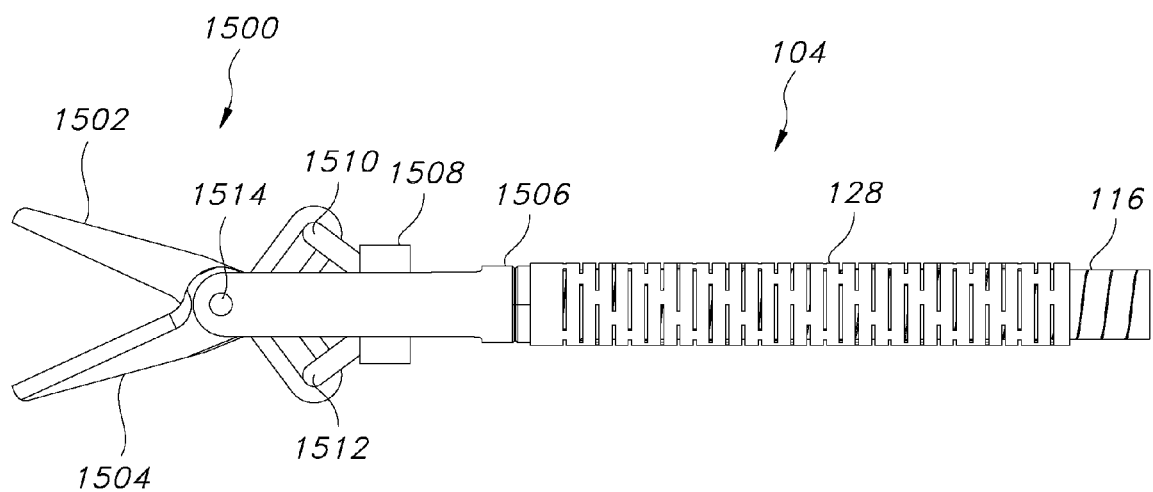
FIG. 15 illustrates an alternative embodiment of the scissors device of FIG. 3 with a link-actuated end effector.

FIG. 15 illustrates another embodiment of the scissors device 100 with a link-actuated end effector 1500. The end effector 1500 may comprise a pair of blade members 1502, 1504. A shuttle 1508 may be coupled to the translating member 116, similar to the shuttle 122. Each blade member 1502, 1504 may be coupled to the shuttle 1508 via links 1510, 1512. When the shuttle 1508 is pushed distally, as shown in FIG. 15, the links 1510, 1512 may push the blade members 1502, 1504 into the open position. As the shuttle 1508 is pulled proximally (e.g., via the translating member 116) the blade members 1502, 1504 may be pulled into the closed position.

Figure 16:
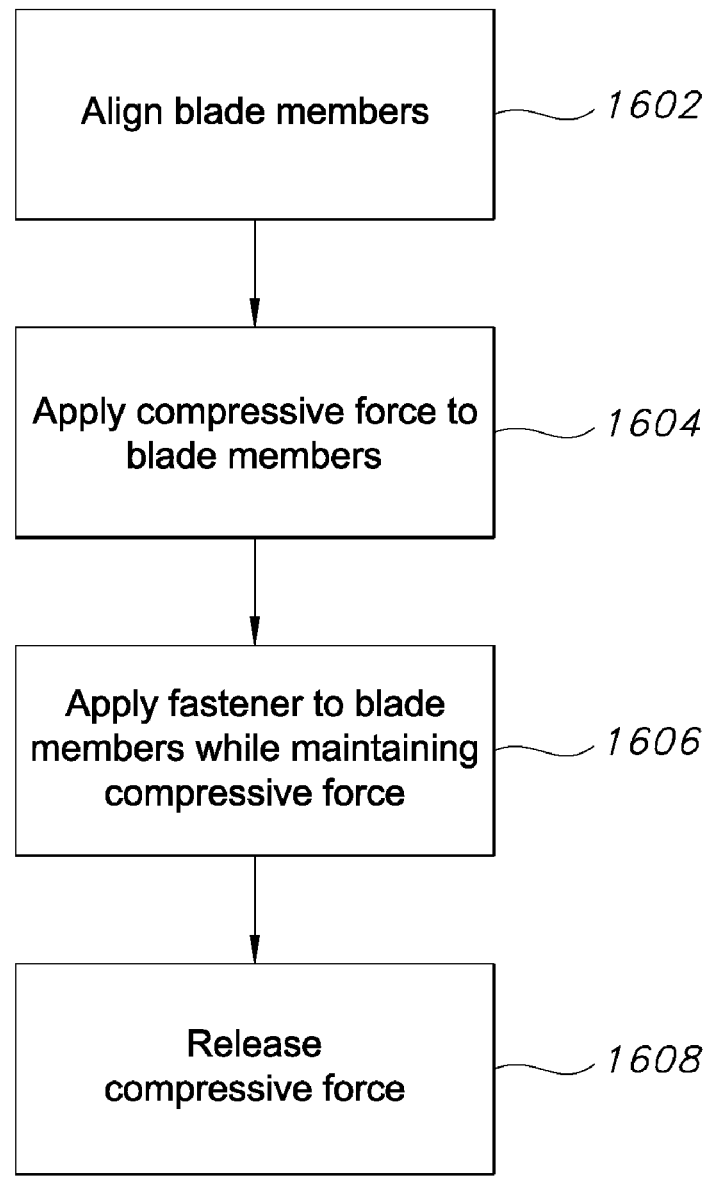
FIG. 16 is a flow chart illustrating one embodiment of a process flow for assembling the blade members of the scissors device of FIG. 1.
Figure 17:
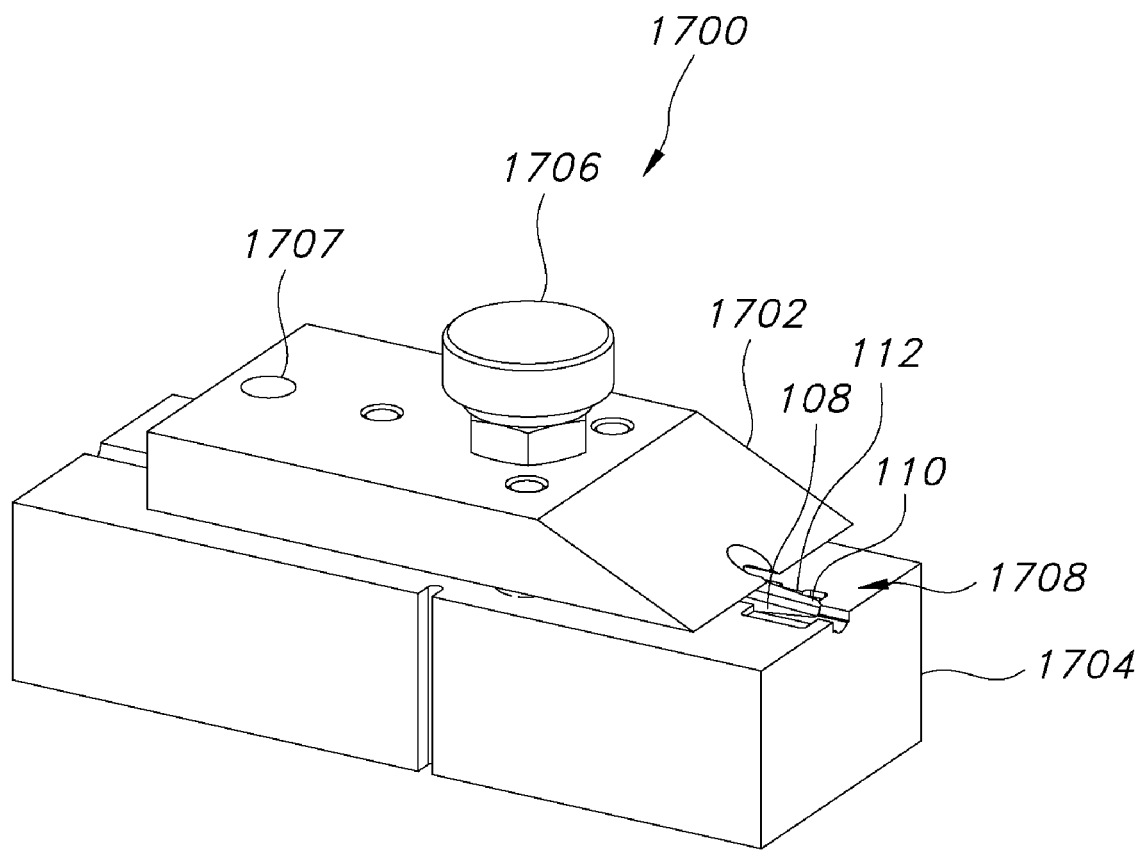
FIG. 17 illustrates one embodiment of a clamp assembly for use in assembling the blade members of the scissors device of FIG. 1.

FIG. 16 is a diagram illustrating one embodiment of a process flow 1600 for assembling the blade members 108, 110 of the scissors device 100. Initially, the blade members 108, 110 and the clevis 112 may be aligned 1602 for assembly. For example, the blade members 108, 110 may be placed between the arms 111, 115 of the clevis 112. According to various embodiments, the blade members 108, 110 and clevis 112 may be aligned 1602 by placing them into a clamp assembly. FIG. 17 illustrates one embodiment of a clamp assembly 1700 in which the blade members 108, 110 and clevis 112 may be aligned. The clamp assembly 1700 may comprise a first clamp member 1702 and a second clamp member 1704. The clamp members 1702, 1704 may be coupled to any suitable kind of clamping mechanism. For example, in the embodiment shown in FIG. 17, the clamping mechanism comprises a threaded screw 1706 that may be coupled to the clamp members 1702, 1704 such that tightening of the threaded screw forces the clamp members 1702, 1704 towards one another. As shown, the clamp member 1704 defines a cavity 1708 shaped to receive the blade members 108, 110. The cavity 1708 may serve to align the blade members 108, 110. According to various embodiments, the clamp member 1702 may have a corresponding cavity (not shown) that may augment and/or replace the cavity 1708.

Figure 18:
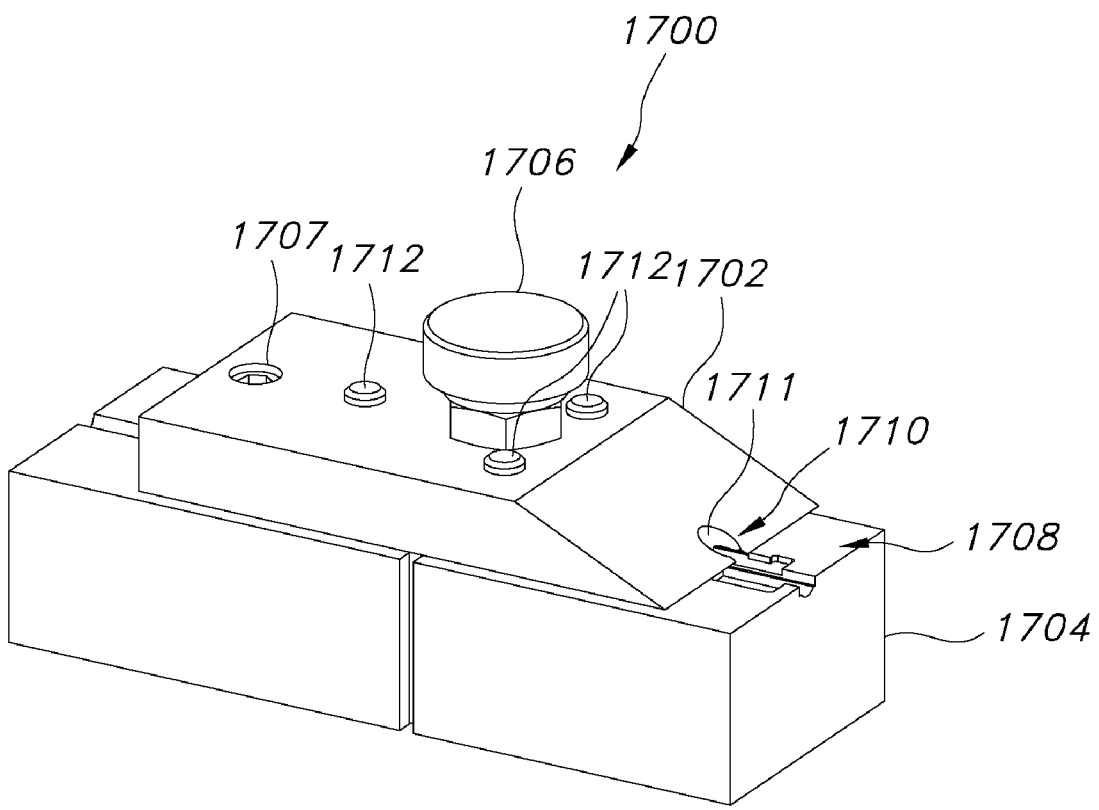
FIG. 18 illustrates one embodiment of the clamp assembly of FIG. 17 with the blade members under compressive force.

Referring back to the diagram 1600, a compressive force may be applied 1604 to the blade members 108, 110 and clevis 112. For example, referring to FIG. 17, the threaded screw 1706 may be rotated, forcing the clamp member 1702 towards the clamp member 1704 to apply the compressive force. FIG. 18 illustrates one embodiment of the clamp assembly 1700 with the blade members 108, 110 and clevis 112 under compressive force. Again referring to FIG. 16, a fastener may be applied 1606 to the blade members 108, 110 and clevis 112 while maintaining the compressive force. The fastener may be applied 1606, for example, to the pivot point 130 (see FIG. 4). The fastener may be any suitable fastener type. For example, the fastener may be a rivet or a screw. In various embodiments, the fastener may comprise a pin welded to the blade members 108, 110 and/or clevis 112 at the pivot point. For example, the pin (not shown) may be laser welded. One or both of the clamp members 1702, 1704 may be configured to allow access to the pivot point 130 for installing the fastener. For example, the clamp member 1702 defines an access opening 1710 over the point where the pivot point 130 of the blade members 108, 110 is located. In the embodiment shown in FIG. 17, the access opening 1710 takes the form of a notch in the clamp member 1702. The notch 1710 may have a beveled edge 1711 as shown to allow greater access through to the pivot point 130 during use. The compressive force may be released 1608. When the compressive force is released 1608, the fastener may serve to maintain the blade members 108, 110 in compression. Reciprocally, the blade members 108, 110 may maintain the fastener in tension.

Figure 19:
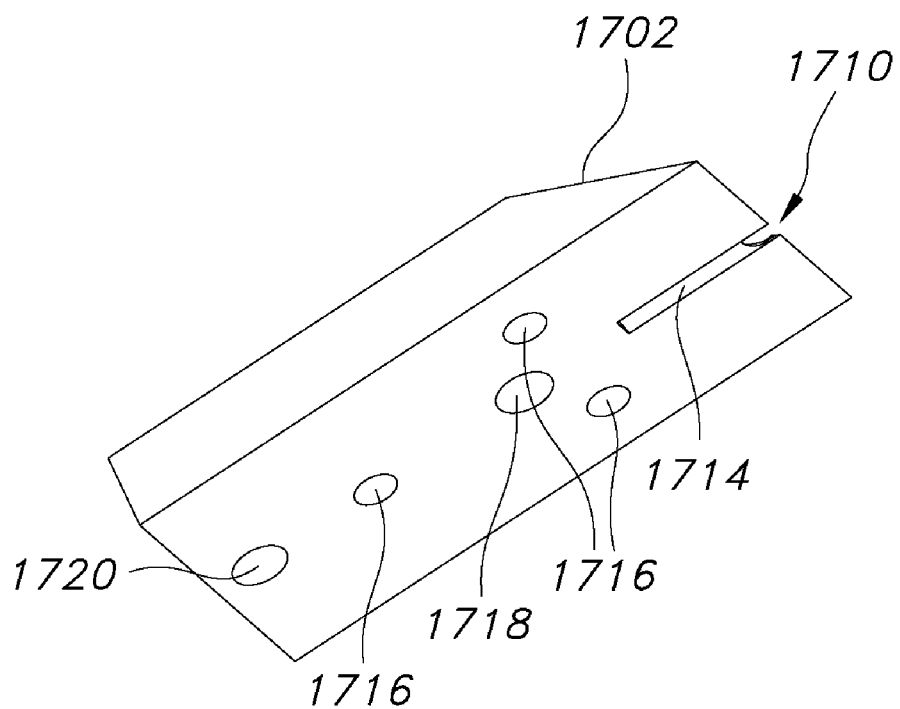
FIG. 19 illustrates one embodiment of a clamp member of the clamp assembly of FIG. 17.

Referring again to FIG. 18, the clamp assembly 1700 may comprise one or more guide pins 1712. The first clamp member 1702 may slide along the guide pins 1712 as the clamp assembly 1700 is opened and closed. An optional set screw 1707 may serve to stabilize the clamp members 1702, 1704. FIG. 19 illustrates one embodiment of the clamp member 1702. As illustrated, the clamp member 1702 may comprise a cavity 1714 for receiving a portion of one or both of the blade members 108, 110. Guide holes 1716 may receive the guide pins 1712. A threaded set screw hole 1720 may receive the set screw 1707. A threaded hole 1718 may receive the threaded screw 1706. A corresponding hole (not shown) may be defined by the clamp member 1704. Accordingly, rotation of the threaded screw 1706 may force the clamp member 1702 towards the clamp member 1704.

Figure 20:
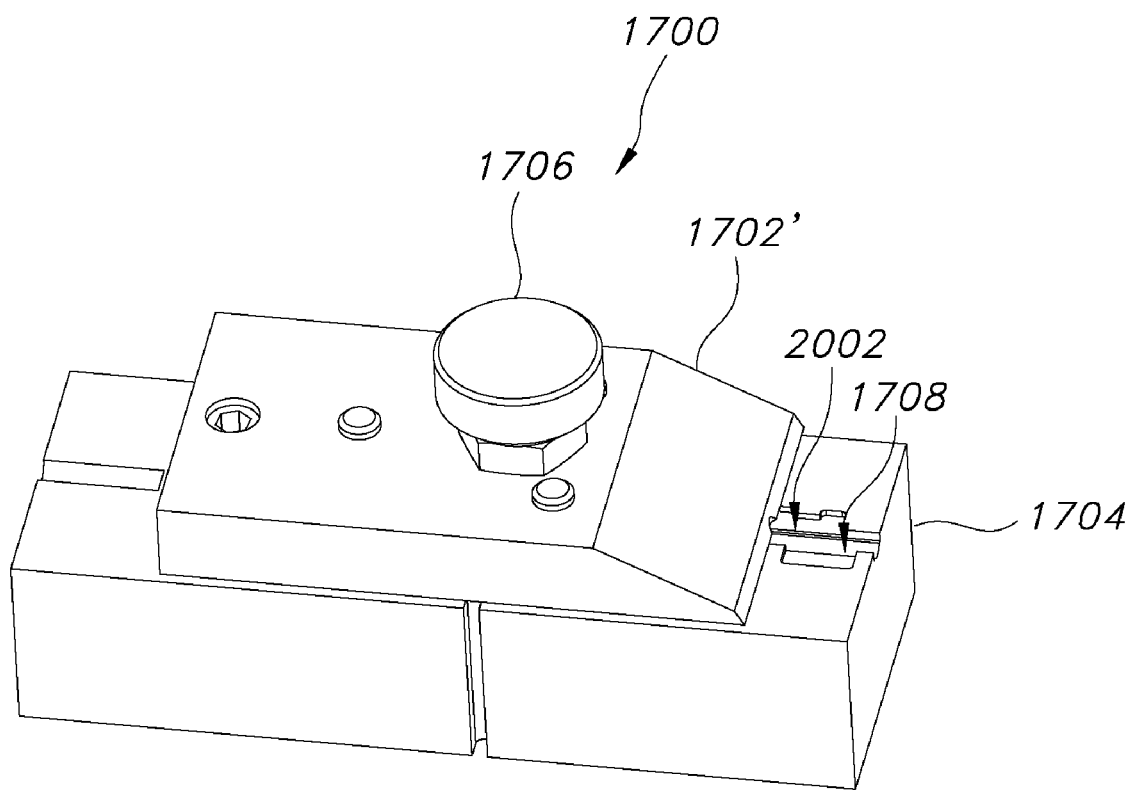
FIG. 20 illustrates another embodiment of the clamp assembly of FIG. 17 having an alternate clamp member.
Figure 21:
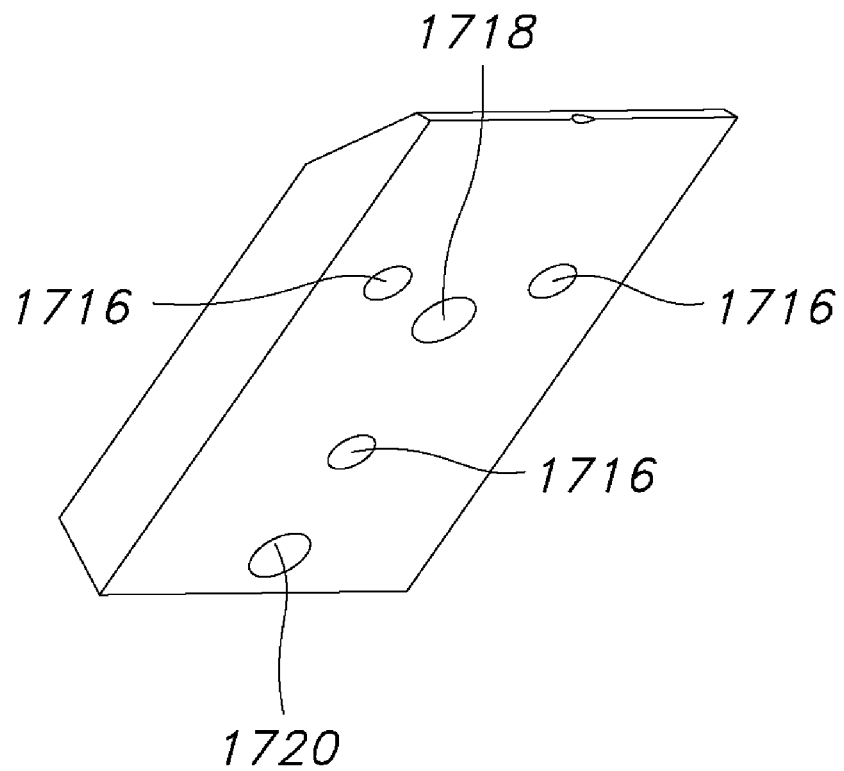
FIG. 21 illustrates one embodiment of the alternate clamp member of FIG. 20.

FIG. 20 illustrates another embodiment of the clamp assembly 1700 comprising an alternate clamp member 1702'. The clamp member 1702' may be shorter than the clamp member 1702. This may allow the clamp member 1702' to expose more of the cavity 1708 than the clamp assembly 1702. In turn, this may allow the clamp member 1702' to have a smaller access opening or notch 2002. FIG. 21 illustrates one embodiment of the alternate clamp member 1702'. The clamp member 1702' may comprise guide holes 1716, a set screw hole 1720 and a threaded hole 1718 similar to the clamp member 1702. As illustrated, however, the clamp member 1702' may lack a cavity for receiving all or a portion of the blade members 108, 110. It will be appreciated that the clamp assembly 1700 may be manually or automatically operated. For example, assembly personal may actuate the clamp by manually turning the threaded screw 1706. Also, in some embodiment the screw 1706 may be actuated by an electric or other motor (not shown).

Figure 22:
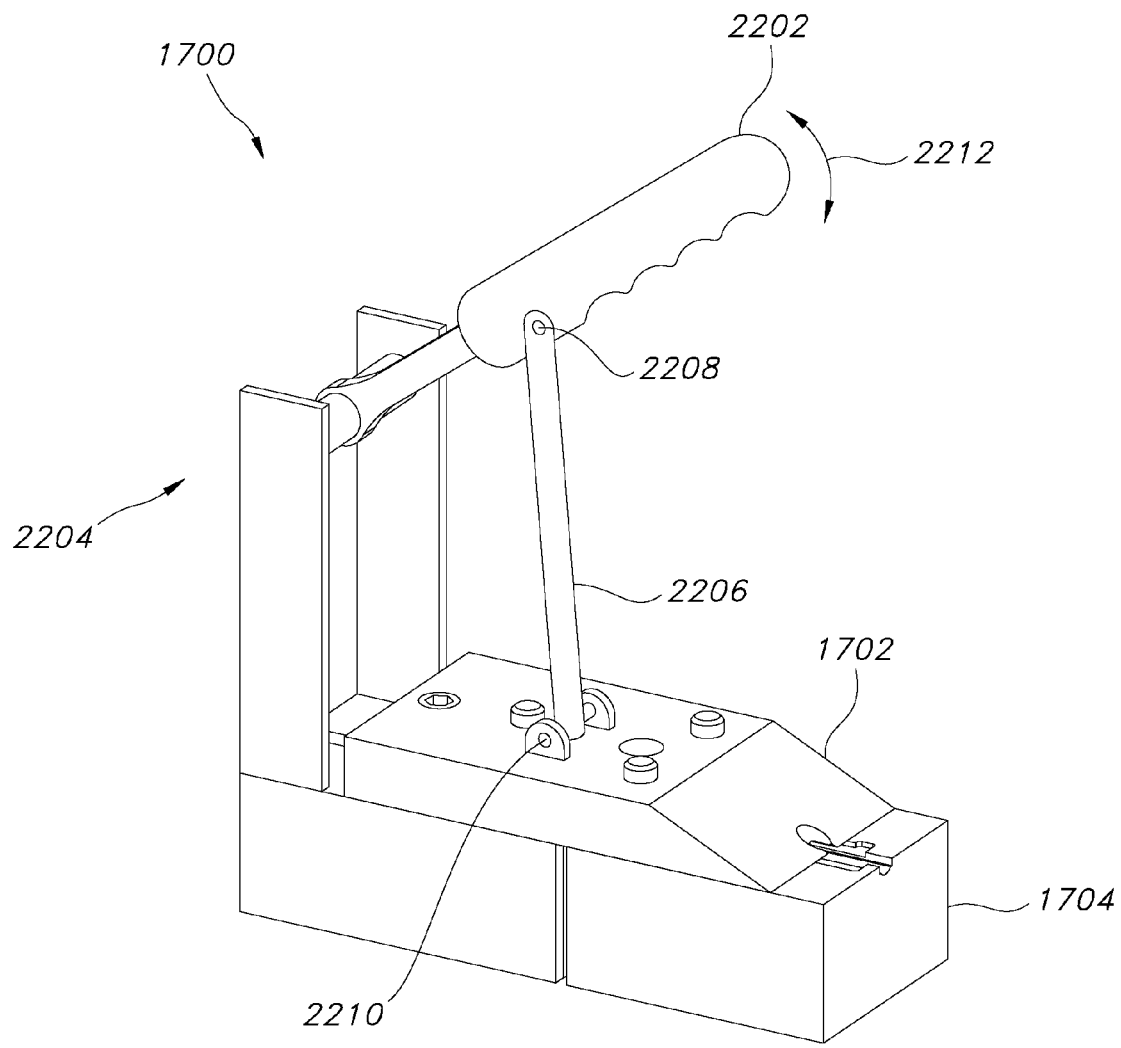
FIG. 22 illustrates one embodiment of the clamp assembly of FIG. 17 with a lever clamp mechanism.

The clamp mechanism of the clamp assembly 1700 described above comprises a threaded screw 1706. It will be appreciated that any other suitable manual or automatic clamp mechanism may be used. For example, FIG. 22 illustrates one embodiment of the clamp assembly 1700 with a lever clamp mechanism. A lever frame 2204 may support a lever bar 2202, which may be pivot about the frame 2204 as shown by arrow 2212. The lever bar 2202 may be pivotably coupled to a link 2206 at pivot point 2208. The link 2206, in turn, may be pivotably coupled to the clamp member 1702 at pivot point 2210. To operate the clamp assembly 1700 as shown in FIG. 22, assembly personnel may rotate the lever bar 2202 towards the clamp member 1702 along arrow 2212. This may force the clamp member 1702 towards the clamp member 1704 as described above. The lever bar 2202 may be manually actuated, for example, directly by assembly personnel, or may be automatically actuated.

Figure 23:
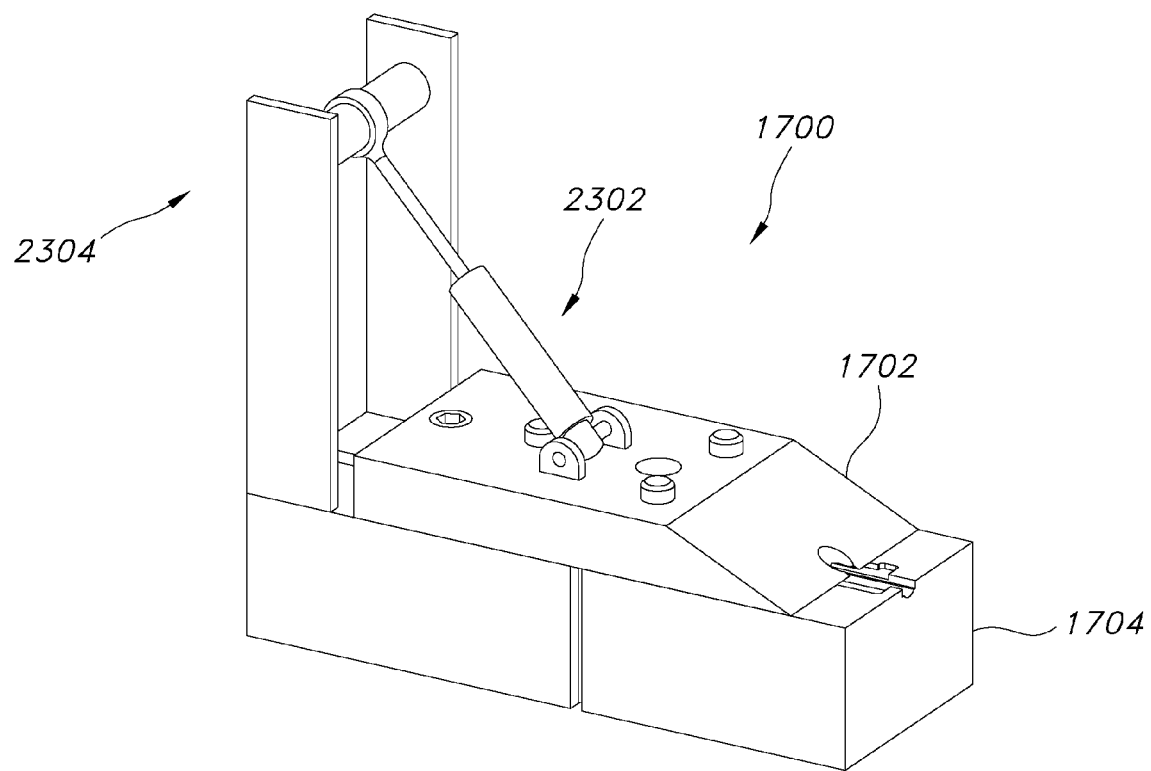
FIG. 23 illustrates another embodiment of the clamp assembly of FIG. 27 with a hydraulic or pneumatic clamp mechanism.

FIG. 23 illustrates another embodiment of the clamp assembly 1700 with a hydraulic or pneumatic clamp mechanism. As shown, cylinder frame 2304 may be pivotably coupled to a cylinder 2302, which may be a pneumatic or hydraulic cylinder. When the cylinder 2302 is activated, it may extend, providing the compressive force between the clamp members 1702, 1704. The cylinder 2302 may be activated, for example, by a hydraulic or pneumatic compressor (not shown) which may be manually and/or automatically actuated.

In various embodiments, surgical instruments utilizing various embodiments of the scissors device 100 may be employed in conjunction with a flexible endoscope, such as a GIF-100 model available from Olympus Corporation, for example. In at least one such embodiment, the endoscope, a laparoscope, or a thoracoscope, for example, may be introduced into the patient trans-anally through the colon, the abdomen via an incision or keyhole and a trocar, or trans-orally through the esophagus, or trans-vaginally through the cervix, for example. These devices may assist the clinician to guide and position the scissors device 100 near the tissue treatment region to treat diseased tissue on organs such as the liver, for example. In another embodiment, these devices may be positioned to treat diseased tissue near the gastrointestinal (GI) tract, esophagus, and/or lung, for example. In various embodiments, the endoscope may comprise a flexible shaft where the distal end of the flexible shaft may comprise a light source, a viewing port, and at least one working channel. In at least one such embodiment, the viewing port may transmit an image within its field of view to an optical device such as a charge coupled device (CCD) camera within the endoscope, for example, so that an operator may view the image on a display monitor (not shown).

It will be appreciated that the terms "proximal" and "distal" are used herein with reference to a clinician manipulating an end of an instrument extending from the clinician to a surgical site (e.g., through a trocar, through a natural orifice, through an open surgical site). The term "proximal" refers to the portion closest to the clinician, and the term "distal" refers to the portion located away from the clinician. It will be further appreciated that for conciseness and clarity, spatial terms such as "vertical," "horizontal," "up," and "down" may be used herein with respect to the drawings. However, surgical instruments are used in many orientations and positions, and these terms are not intended to be limiting and absolute.

While several embodiments have been illustrated and described, and while several illustrative embodiments have been described in considerable detail, the described embodiments are not intended to restrict or in any way limit the scope of the appended claims to such detail. Additional advantages and modifications may readily appear to those skilled in the art. Those of ordinary skill in the art will readily appreciate the different advantages provided by these various embodiments.

While several embodiments have been described, it should be apparent, however, that various modifications, alterations and adaptations to those embodiments may occur to persons skilled in the art with the attainment of some or all of the advantages of the embodiments. For example, according to various embodiments, a single component may be replaced by multiple components, and multiple components may be replaced by a single component, to perform a given function or functions. The described embodiments are therefore intended to cover all such modifications, alterations and adaptations without departing from the scope of the appended claims.

The devices disclosed herein may be designed to be disposed of after a single use, or they may be designed to be used multiple times. In either case, however, the device may be reconditioned for reuse after at least one use. Reconditioning may include a combination of the steps of disassembly of the device, followed by cleaning or replacement of particular pieces, and subsequent reassembly. In particular, the device may be disassembled, and any number of particular pieces or parts of the device may be selectively replaced or removed in any combination. Upon cleaning and/or replacement of particular parts, the device may be reassembled for subsequent use either at a reconditioning facility, or by a surgical team immediately prior to a surgical procedure. Those of ordinary skill in the art will appreciate that the reconditioning of a device may utilize a variety of different techniques for disassembly, cleaning/replacement, and reassembly. Use of such techniques, and the resulting reconditioned device, are all within the scope of this application.

Preferably, the embodiments described herein will be processed before surgery. First a new or used instrument is obtained and, if necessary, cleaned. The instrument may then be sterilized. In one sterilization technique, the instrument is placed in a closed and sealed container, such as a plastic or TYVEK® bag. The container and instrument are then placed in a field of radiation that may penetrate the container, such as gamma radiation, x-rays, or higher energy electrons. The radiation kills bacteria on the instrument and in the container. The sterilized instrument may then be stored in the sterile container. The sealed container keeps the instrument sterile until it is opened in the medical facility.

Any patent, publication, or other disclosure material, in whole or in part, that is said to be incorporated by reference herein is incorporated herein only to the extent that the incorporated materials do not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The embodiments are not to be construed as limited to the particular embodiments disclosed. The embodiments are therefore to be regarded as illustrative rather than restrictive. Variations and changes may be made by others without departing from the scope of the claims. Accordingly, it is expressly intended that all such equivalents, variations and changes that fall within the scope of the claims be embraced thereby.

In summary, numerous benefits have been described which result from employing the embodiments described herein. The foregoing description of the one or more embodiments has been presented for purposes of illustration and description. It is not intended to be exhaustive or limiting to the precise form disclosed. Modifications or variations are possible in light of the above teachings. The one or more embodiments were chosen and described in order to illustrate principles and practical applications to thereby enable one of ordinary skill in the art to utilize the various embodiments and with various modifications as are suited to the particular use contemplated. It is intended that the claims submitted herewith define the overall scope.

What is claimed is:

1. A method of forming surgical scissors comprising first and second blade members joined between first and second arms of a clevis at a pivot point, wherein the first and second blade members and the first and second arms each define pin holes at the pivot point, the method comprising:

positioning the first and second blade members of the surgical scissors and the clevis such that the pin holes of the first and second blades align with the pin holes of the first and second arms of the clevis;

applying a compressive force to the first and second blade members and the clevis, wherein the compressive force is directed to force the first and second blade members towards one another between the first and second arms of the clevis, wherein applying the compressive force comprises:

placing at least a portion of the first blade member and at least a portion of the second blade member between a first clamp member and a second clamp member, and compressing first and second clamp members towards one another with the first and second blade members therebetween; and while maintaining the compressive force, applying a fastener through the pin holes of the first and second blade members and the first and second arms of the clevis, wherein the fastener is configured to join the first blade member and the second blade member, and wherein applying the fastener comprises at least one action selected from the group consisting of:

applying the fastener through at least a portion of the first clamp member; and applying the fastener around at least a portion of the first clamp member.

2. The method of claim 1, further comprising releasing the compressive force.

3. The method of claim 1, further comprising maintaining the fastener in tension with the first and second arms of the clevis after the compressive force is removed.

4. The method of claim 1, wherein applying the fastener comprises applying at least one fastener selected from the group consisting of a rivet, a pin and a threaded fastener.

5. The method of claim 1, wherein applying the fastener comprises laser welding a pin to the first and second arms of the clevis.

6. The method of claim 1, wherein applying the compressive force comprises:
placing the first and second blade members and the clevis in a clamp; and
engaging the clamp to apply the compressive force.

7. The method of claim 6 wherein applying the fastener comprises applying the fastener through an access opening over the pin holes of the first and second blade members, wherein the access opening is defined by the clamp.

8. The method of claim 6, wherein engaging the clamp comprises actuating a threaded screw.

9. The method of claim 1, wherein the first blade member comprises a first blade end positioned distally from the pin hole of the first blade member and a first cam, positioned proximally from the pin hole of the first blade member, wherein the first cam defines a first cam slot, wherein the second blade member comprises a second blade end positioned distally from the pin hole of the second blade member and a second cam, positioned proximally from the pin hole of the second blade member, and wherein the second cam defines a second cam slot.

10. The method of claim 9, further comprising placing the first and second blade members in mechanical communication with a reciprocating shuttle comprising at least one pin positioned within the first cam slot and the second cam slot such that distally-directed motion of the shuttle causes the first and second blade members to open and proximally-directed motion of the shuttle causes the first and second blade members to close.

11. The method of claim 10, wherein the at least one pin comprises a single pin positioned within the first cam slot and the second cam slot.

12. The method of claim 10, further comprising placing the first and second blade members in mechanical communication with a handle via a flexible shaft and a translating member within the flexible shaft, wherein the translating member is coupled to an actuator of the handle such that placing the actuator in a first position causes the shuttle to translate distally and placing the actuator in a second position causes the shuttle to translate proximally.

13. The method of claim 12, wherein the flexible shaft comprises a slotted hypotube.

14. The method of claim 13, wherein a spatial frequency of slots in the slotted hypotube is higher at a distal portion of the hypotube than at a proximal portion of the hypotube.

15. The method of claim 12, wherein the translating member comprises a slotted hypotube.

16. The method of claim 9, wherein the first blade end and the second blade overlap one another when the first and second blade members are in the open position.

17. The method of claim 16, wherein the overlap is between about 0.127 mm and 0.152 mm.

18. A method of forming surgical scissors comprising first and second blade members joined between first and second arms of a clevis at a pivot point, wherein the first and second blade members and the first and second arms each define pin holes at the pivot point, the method comprising:
positioning the first and second blade members of the surgical scissors and the clevis such that the pin holes of the first and second blades align with the pin holes of the first and second arms of the clevis;
applying a compressive force to the first and second blade members and the clevis, wherein the compressive force is directed to force the first and second blade members towards one another between the first and second arms of the clevis, wherein applying the compressive force comprises:
placing the first and second blade members and the clevis in a clamp; and
engaging the clamp to apply the compressive force; and
while maintaining the compressive force, applying a fastener through the pin holes of the first and second blade members and the first and second arms of the clevis, wherein the fastener is configured to join the first blade member and the second blade member, wherein applying the fastener comprises applying the fastener through an access opening over the pin holes of the first and second blade members, wherein the access opening is defined by the clamp.

19. A method of forming surgical scissors comprising first and second blade members joined between first and second arms of a clevis at a pivot point, wherein the first and second blade members and the first and second arms each define pin holes at the pivot point, the method comprising:
positioning the first and second blade members of the surgical scissors and the clevis such that the pin holes of the first and second blades align with the pin holes of the first and second arms of the clevis;
applying a compressive force to the first and second blade members and the clevis, wherein the compressive force is directed to force the first and second blade members towards one another between the first and second arms of the clevis, wherein applying the compressive force comprises:
placing the first and second blade members and the clevis in a clamp; and
engaging the clamp to apply the compressive force, wherein engaging the clamp comprises actuating a threaded screw; and
while maintaining the compressive force, applying a fastener through the pin holes of the first and second blade members and the first and second arms of the clevis, wherein the fastener is configured to join the first blade member and the second blade member.

20. A method of forming surgical scissors comprising first and second blade members joined between first and second arms of a clevis at a pivot point, wherein the first and second blade members and the first and second arms each define pin holes at the pivot point, wherein the first blade member comprises a first blade end positioned distally from the pin hole of the first blade member and a first cam positioned proximally from the pin hole of the first blade member, wherein the first cam defines a first cam slot, wherein the second blade member comprises a second blade end positioned distally from the pin hole of the second blade member and a second cam positioned proximally from the pin hole of the second blade member, and wherein the second cam defines a second cam slot, the method comprising:
positioning the first and second blade members of the surgical scissors and the clevis such that the pin holes of the first and second blades align with the pin holes of the first and second arms of the clevis;

applying a compressive force to the first and second blade members and the clevis, wherein the compressive force is directed to force the first and second blade members towards one another between the first and second arms of the clevis; and while maintaining the compressive force, applying a fastener through the pin holes of the first and second blade members and the first and second arms of the clevis, wherein the fastener is configured to join the first blade member and the second blade member.

21. The method of claim 20, further comprising placing the first and second blade members in mechanical communication with a reciprocating shuttle comprising at least one pin positioned within the first cam slot and the second cam slot such that distally-directed motion of the shuttle causes the first and second blade members to open and proximally-directed motion of the shuttle causes the first and second blade members to close.

22. The method of claim 21, further comprising placing the first and second blade members in mechanical communication with a handle via a flexible shaft and a translating member within the flexible shaft, wherein the translating member is coupled to an actuator of the handle such that placing the actuator in a first position causes the shuttle to translate distally and placing the actuator in a second position causes the shuttle to translate proximally.

23. The method of claim 22, wherein the flexible shaft comprises a slotted hypotube.

24. The method of claim 23, wherein a spatial frequency of slots in the slotted hypotube is higher at a distal portion of the hypotube than at a proximal portion of the hypotube.

25. The method of claim 22, wherein the translating member comprises a slotted hypotube.

26. The method of claim 21, wherein the at least one pin comprises a single pin positioned within the first cam slot and the second cam slot.

27. The method of claim 20, wherein the first blade end and the second blade overlap one another when the first and second blade members are in the open position.

28. The method of claim 27, wherein the overlap is between about 0.127 mm and 0.152 mm.

\* \* \* \* \*